US006258196B1

(12) United States Patent
Suzuki et al.

(10) Patent No.: US 6,258,196 B1
(45) Date of Patent: *Jul. 10, 2001

(54) POROUS COMPOSITE SHEET AND PROCESS FOR THE PRODUCTION THEREOF

(75) Inventors: Migaku Suzuki, Kamakura; Hiroaki Fukui, Kawaguchi, both of (JP)

(73) Assignee: Paragon Trade Brands, Inc., Norcross, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,450
(22) PCT Filed: Jul. 9, 1996
(86) PCT No.: PCT/JP96/01893
§ 371 Date: Jan. 9, 1998
§ 102(e) Date: Jan. 9, 1998
(87) PCT Pub. No.: WO97/02946
PCT Pub. Date: Jan. 30, 1997

(30) Foreign Application Priority Data

Jul. 10, 1995 (JP) ................................................ 7-6981 U
Sep. 19, 1995 (JP) ................................................ 7-239595

(51) Int. Cl.[7] ............................ B32B 31/06; B32B 31/26
(52) U.S. Cl. .......................... 156/176; 156/290; 156/296; 156/308.2

(58) Field of Search .................................... 428/182, 198; 442/340, 351, 364, 370, 382, 384, 385, 387, 388, 392, 408, 400; 156/290, 308.2, 176, 296

(56) References Cited

U.S. PATENT DOCUMENTS

| 5,273,596 | * | 12/1993 | Newkirk ................................ 156/73.2 |
| 5,306,545 | * | 4/1994 | Shirayanagi et al. ................. 428/198 |

FOREIGN PATENT DOCUMENTS

| 61-2854 | * | 1/1986 | (JP) . |
| 1-272449 | * | 1/1989 | (JP) . |
| 2-177958 | * | 7/1990 | (JP) . |
| 5-1711556 | * | 7/1993 | (JP) . |
| 5-192365 | * | 8/1993 | (JP) . |
| 7-42057 | * | 2/1995 | (JP) . |
| 7-155594 | * | 6/1995 | (JP) . |
| 7-155595 | * | 6/1995 | (JP) . |

* cited by examiner

Primary Examiner—Blaine Copenheaver
(74) Attorney, Agent, or Firm—Hunton & Williams

(57) ABSTRACT

A sintered porous composite sheet, comprising an A/B-component layer in which the A-component layer is easily fusible and the B-component layer has a relatively higher thermal stability as compared with the A-component layer. The layers are superposed and sintered. The A-component layer comprises a hydrophilic material, the B-component layer comprises a hydrophobic material, and the A-component and B-component may include a common material comprising an easily fusible material. The porous composite sheet is air and moisture permeable, and is readily adaptable for use in sanitary and medical applications.

26 Claims, 27 Drawing Sheets

FIG. 2
(a) 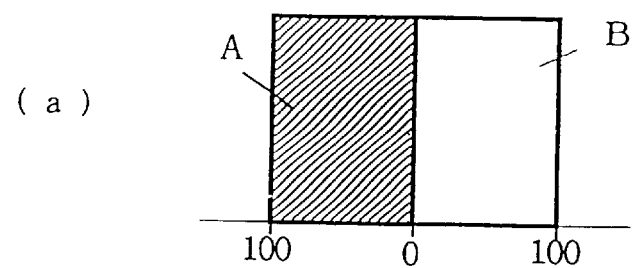
(b) 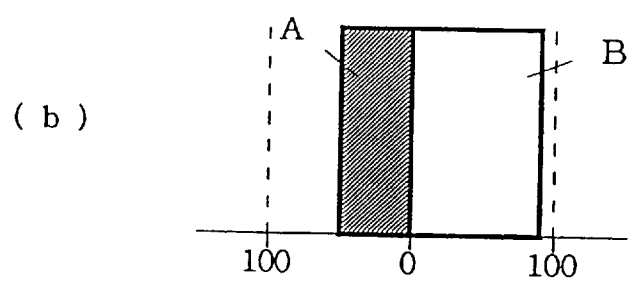
(c) 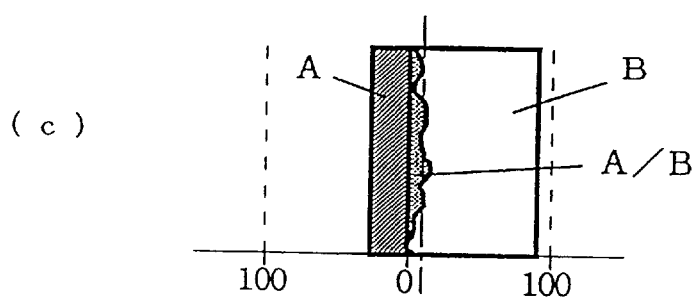
(d) 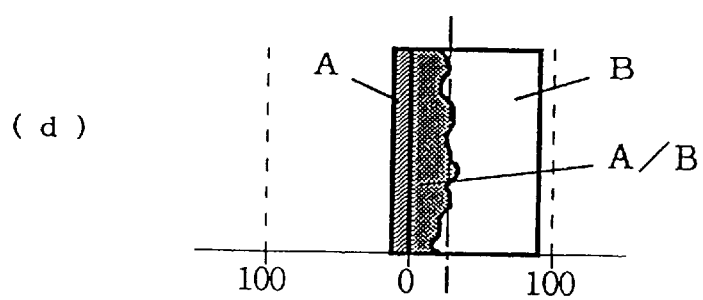
(e) 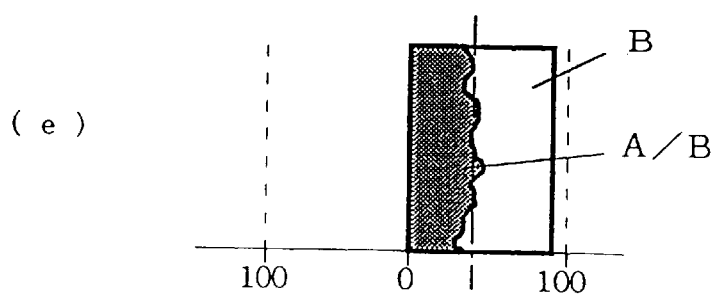

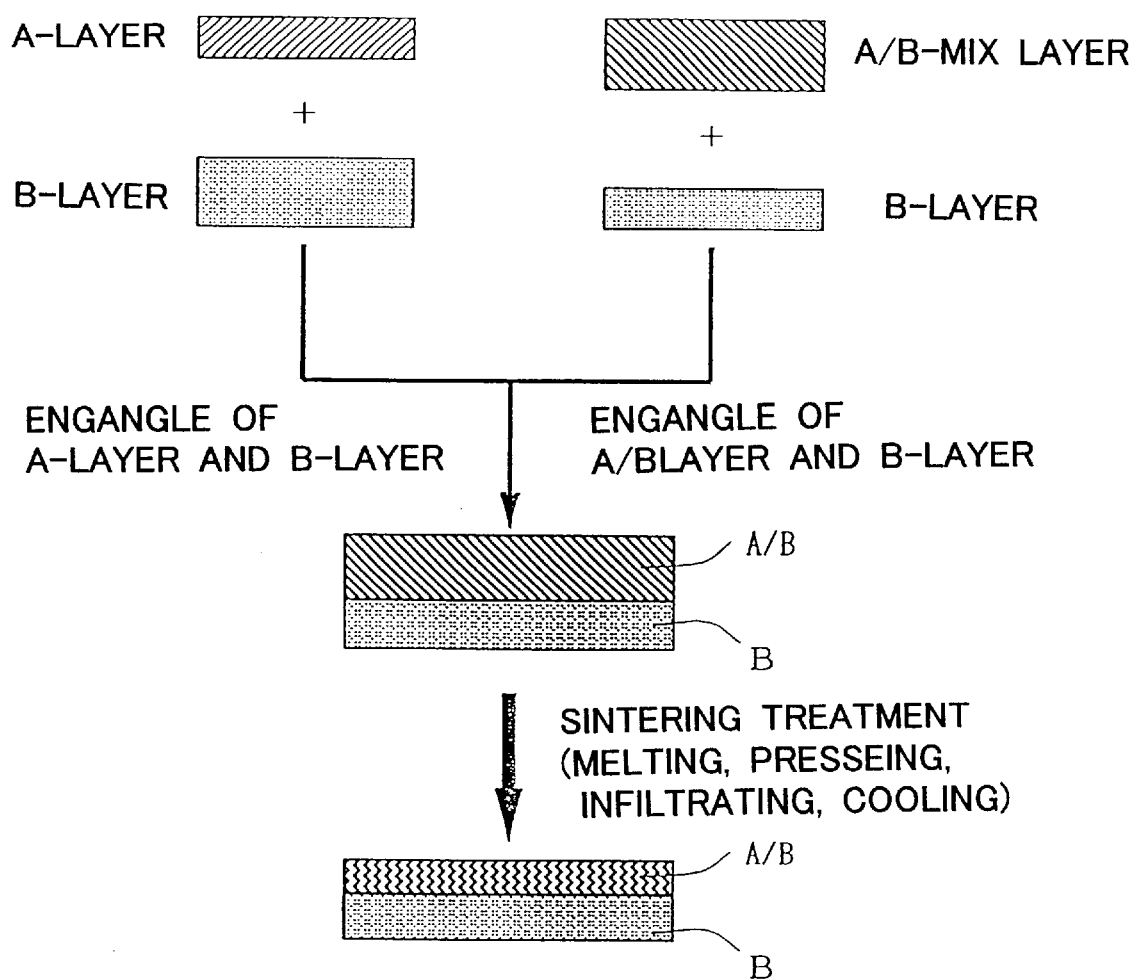

FIG. 5
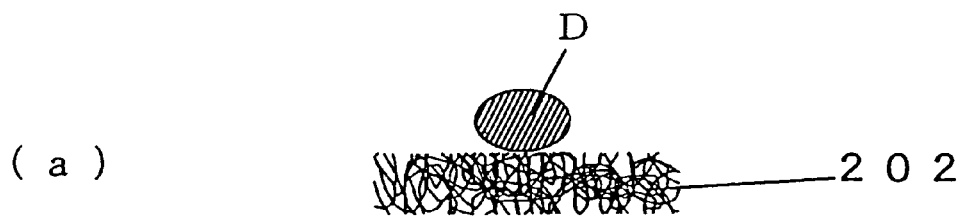
(a)
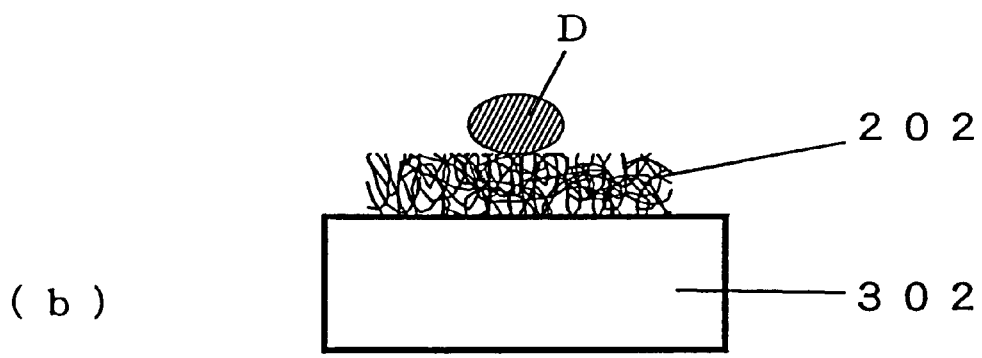
(b)
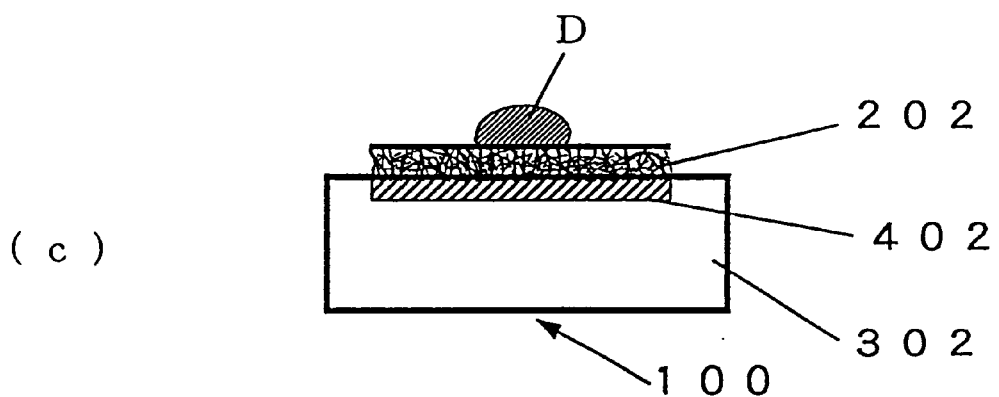
(c)
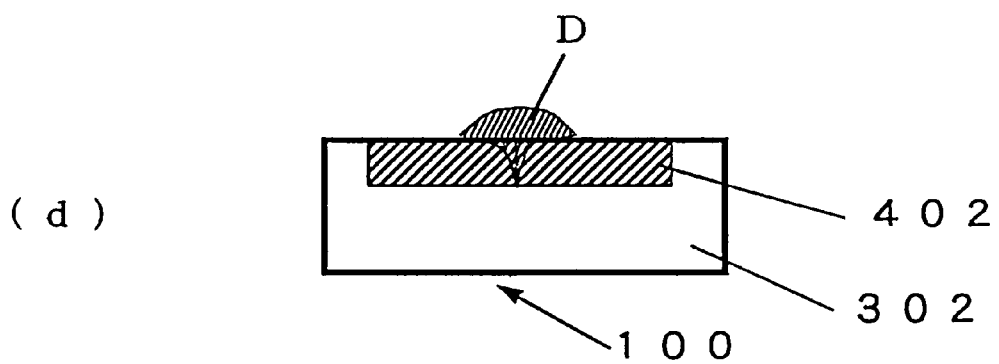
(d)

FIG. 6
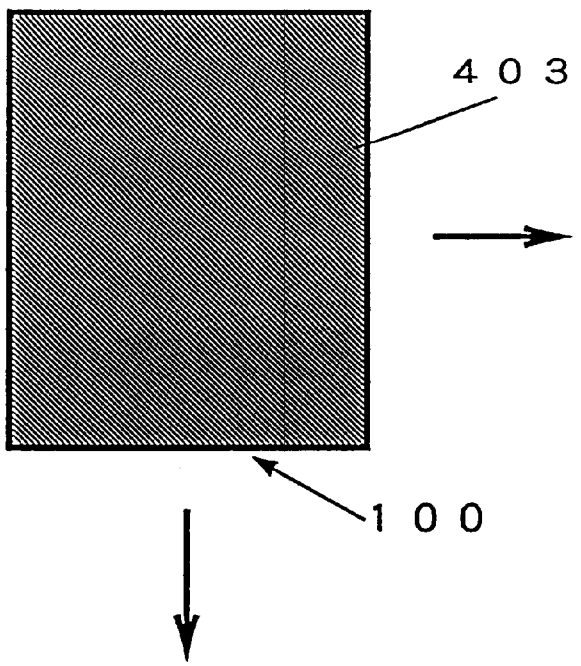
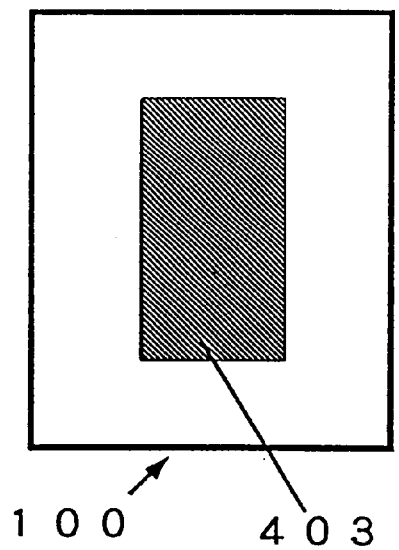
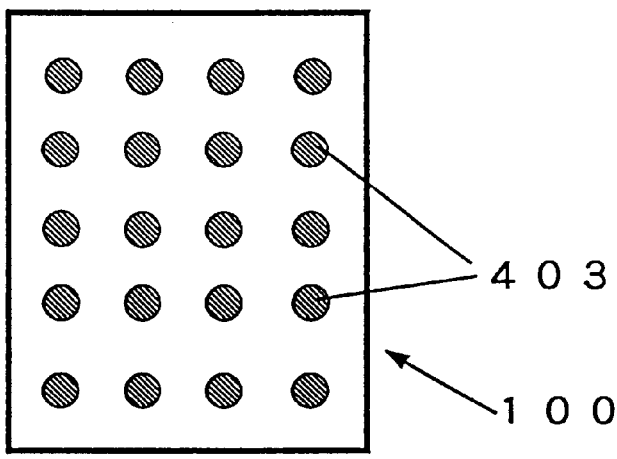

ABSORBING, SWELLING (A)

POROUS COMPOSITE SHEET AND PROCESS FOR THE PRODUCTION THEREOF

FIELD OF THE INVENTION

The present invention relates to a sintered porous composite sheet having a multilayered structure, and more particularly relates to a sintered porous composite sheet which is air-permeable or moisture permeable and is useful as a top sheet or back sheet for a sanitary article or medical applications.

BACKGROUND OF THE INVENTION

Generally, sheet articles having a porous structure may be classified into the following five groups according to pore size:

| Pore Size ($\mu$m) | Materials | Uses |
| --- | --- | --- |
| 0.01–0.1 | Gas-Barrier Film | Gas Permeability |
| 0.1–1.0 | Film Filter | Water-Vapor Permeability |
| 1.0–10.0 | Meltblown, Flash-spinning Web | Biobarrier |
| 10.0–100 | Conventional Nonwoven Fabric | Porous Articles |
| 100–1000 | Perforated Nonwoven Fabric | Perforated Articles |

Among these porous sheets, those having a pore size of about 10 $\mu$m or less are generally referred to as "microporous materials." Such sheets are produced according to special techniques for forming films, such as an extracting method, a phase separation method or a method which comprises adding an inorganic powder in a high concentration and stretching the film in a biaxial direction. Microporous sheets are widely applied to special filters, air permeable water-proof sports wear and the like. Microporous sheets are also used in composites in conjunction with nonwoven fabric and/or woven fabric.

For example, Japanese Patent KOKAI (Laid-Open) No. 14023/89 discloses a method of producing a porous sheet. There, a film of a crystalline polyolefine resin, a rubber-like polymer and an inorganic filler are first drawn and then hot-crimped to orient the film into a mesh-like sheet. The mesh-like sheet is then fixed and thermally contracted. The lack of uniformity of the mesh-like sheet causes deficient performance.

Further, porous sheets manufactured according to the conventional methods are generally hard and fragile. Consequently, porous sheets are not usually satisfactory as a high performance material for application in sanitary articles, medical articles, etc.

These and other drawbacks of the prior art are sought to be overcome by the porous composite sheet of the preferred embodiments.

SUMMARY OF THE INVENTION

It is an object of the present invention to provide a high-performance porous sheet in which the foregoing defects are eliminated, and which is readily applicable to sanitary articles, medical articles, etc.

It is another object of the present invention to provide a method of producing such a porous sheet.

According to the preferred embodiments of the present invention, a sintered porous composite sheet preferably has A/B component layers in which the A-component layer is easily fusible and the B-component layer is more thermally stable than the A-component layer. The layers are preferably sintered together. When the A-component layer and the B-component layer are sintered together to produce the A/B component layers, the easily fusible properties of the A-component layer and the relatively high thermal stability of the B-component layer are realized.

Furthermore, according to the preferred embodiments of the present invention, there is disclosed a method of producing a sintered porous composite sheet, characterized in that a first porous layer and a second porous layer are superposed, wherein the first layer is easily fusible and the second layer has a relatively higher thermal stability as compared with the first layer. The first and second porous layers preferably are thermal treated under pressure and under such temperature conditions that the A-component layer is molten, while the B-component layer is stable. The melted A-component layer is applied to the B-component layer, and then allowed to cool and solidify. A three layer composite is obtained: an A-component layer which is molten and resolidified, an A/B component layer, and a B-component layer having low thermal deformation.

Moreover, according to the preferred embodiments of the present invention, there is disclosed a water-permeable composite sheet comprising a hydrophilic first layer and a second layer which is positioned so as to be adjacent to said first layer;

said first layer and said second layer contain a common component comprising an easily fusible material; and said first layer and said second layer are bonded to each other at sintered sites which are formed by mutually sintering said common component which is contained in both layers, whereby said composite sheet is water-permeable at said sintered sites.

The sintered sites may be formed substantially entirely over the surface of the composite sheet, or may be formed in any pattern over a portion of the surface. The common material which is contained in the first and second layers is preferably an easily fusible fiber. Alternatively, bicomponent fibers having an easily fusible sheath and a higher thermally stable core can be advantageously used as the common material. Furthermore, according to the preferred embodiments of the present invention, there is disclosed an absorbent product comprising a liquid-impermeable outer-sheet, a water-permeable composite inner sheet, and an absorbent core positioned between the outer sheet and the inner sheet.

The inventions of the preferred embodiments are in part founded on the unexpected discovery that a preformed porous layer may be hot-pressed to form a porous sheet having properties entirely different from those disclosed in Japanese Patent KOKAI (Laid-Open) No. 14023/89. Namely, according to the preferred embodiments of the present invention, two porous layers having different fusible properties are combined so that at least part of a fusible layer, i.e., a porous layer which has easily fusible properties, infiltrates voids of a porous layer which has a higher thermal stability. The layers are subsequently press bonded to each other and cooled. Accordingly, a sintered composite sheet which is porous in an extremely large range and has a variety of advantageous properties is obtained by selecting preferred materials and the conditions of the sintering. Table 1 enumerates some of the possibilities:

TABLE 1

| Materials Constituting Porous First Layer | Materials Constituting Porous Second Layer | Functional Material Obtained by Sintering |
| --- | --- | --- |
| Up to 0.01 d PP/PE Microfibrils | Hydrophobic, Water-repellent | Waterproof Material having Air-permeability and Moisture-permeability |
| Up to 0.1 d PP/PE Extra Fine Fibers | Cotton-Spunlace Nonwoven Fabric | Surgical gown having Biobarrier properties |
| Up to 1 d PP Spunbond Nonwoven Fabric | PVA Sponge | Dustproof Controlling Material |
| PE/PET - Bicomponent-Spunbond Nonwoven Fabric | Thermally bonded Nonwoven Fabric containing Hydrophilicated PE/PET-Bicomponent Fibers | Surface Material |

At its basic level, the present invention comprises two bonded porous layers. The first layer is a microporous structure. The A-component layer infiltrates the voids of the second layer to form sintered portions of both the A-component and the B-component. In order to maintain dimensional stability without losing the porous structure of the B-component and without causing thermal contraction, etc., when the A-component is heated to a sintering state, the difference between the melting point of the A-component and the B-component is desirably 30° C. or more, and more desirably 50° C. or more. Preferably, the A-component comprises easily fusible materials, for example, polymeric materials such as PE, PP, PET and derivatives thereof, SEBS, SIS, and SEPS, and the combinations thereof. Suitable, slightly or nonfusible materials can be selected from the group consisting of cellulose, polyurethane, polyvinyl alcohol, polyphenol, polyacrylonitrile, polymeric polyester and nylon materials and derivatives thereof, which have a relatively higher melting point than the A-component. Any combination of these materials having a generally higher melting temperature than the A-component can be used in the practice of this invention.

In the present specification, the term "porous material" means a material having a specific gravity of about 0.2 g/cm$^3$ or less, and more preferably about 0.1 g/cm$^3$ or less. As it may become difficult to hot-melt and compress a material having a specific gravity of 0.02 g/cm$^3$ or less, care must be taken.

Preferably, the first porous layer comprises either a meltblown nonwoven fabric, a wet-formed sheet of synthetic pulp, a foam extruded net, a molten extruded high-fibrillated net, a spunbond nonwoven fabric, a carded nonwoven fabric, or a sheet material obtained by any combination of the foregoing. The second porous layer preferably comprises a foam sheet, an air-laid wood-pulp sheet, a fiber mat, tissue paper, rayon or cotton-web, a cellulose web which was made into a CMC, a polyacrylonitrile-fiber web which was partially hydrolyzed, a synthetic-fiber web such as polyester or nylon, which has a relatively higher melt-concentration in combination with the A-component; and a mixed material thereof. The combination of a first layer comprising a hydrophobic material and a second layer comprising a hydrophilic material is most suitable for applications in sanitary and medical articles.

In the sintered porous composite sheet of the present invention, the heating and pressing steps preferably follow one of the three following modes in order to obtain the various degrees of sintering:

(a) The first porous layer is made into a film to form three layers comprising an A-component layer, A/B component mixed layer and a B-component layer. The A-component layer is divided into a layer comprising the A-component alone, and an A/B-component layer in which a portion of the A-component layer is shifted into the B-component layer. Preferably about 50% or more by weight of the A-component layer shifts into the B-component layer, and more preferably 70% or more so as to form the A/B-component layer.

(b) Almost all of the A-component layer is shifted into the B-component layer to form a sintered composite sheet comprising an A/B-component layer and a B-component layer.

(c) Almost all of the A-component layer and almost all of the B-component layer are mixed with each other to form sintered composite sheet comprising an A/B-component layer only.

The method for forming a sintered A/B component layer comprises superposing the A-component layer and the B-component layer, heat melting the A-component layer, and pressing the A-component layer into the B-component layer. Alternatively, the A/B-component layer is formed, and then the A-component layer is sintered and pressed into the B-component layer.

These and other objects, features and advantages of the preferred embodiments will become apparent when the specification is read in conjunction with the drawing figures.

BRIEF DESCRIPTION OF THE DRAWINGS

FIG. 2 is a schematic diagram which illustrates the transition of the two component layers in a sintered porous composite sheet of the present invention.

FIG. 3A is a schematic diagram which illustrates a process by which a sintered porous composite sheet of the present invention is produced.

FIGS. 5A–D are schematic diagrams of a process by which a sintered porous composite sheet of the present invention is produced.

FIGS. 6A–C are plan views which illustrate a first embodiment of a sintered porous composite sheet of the present invention.

DETAILED DESCRIPTION OF THE PREFERRED EMBODIMENTS

Figure 1:
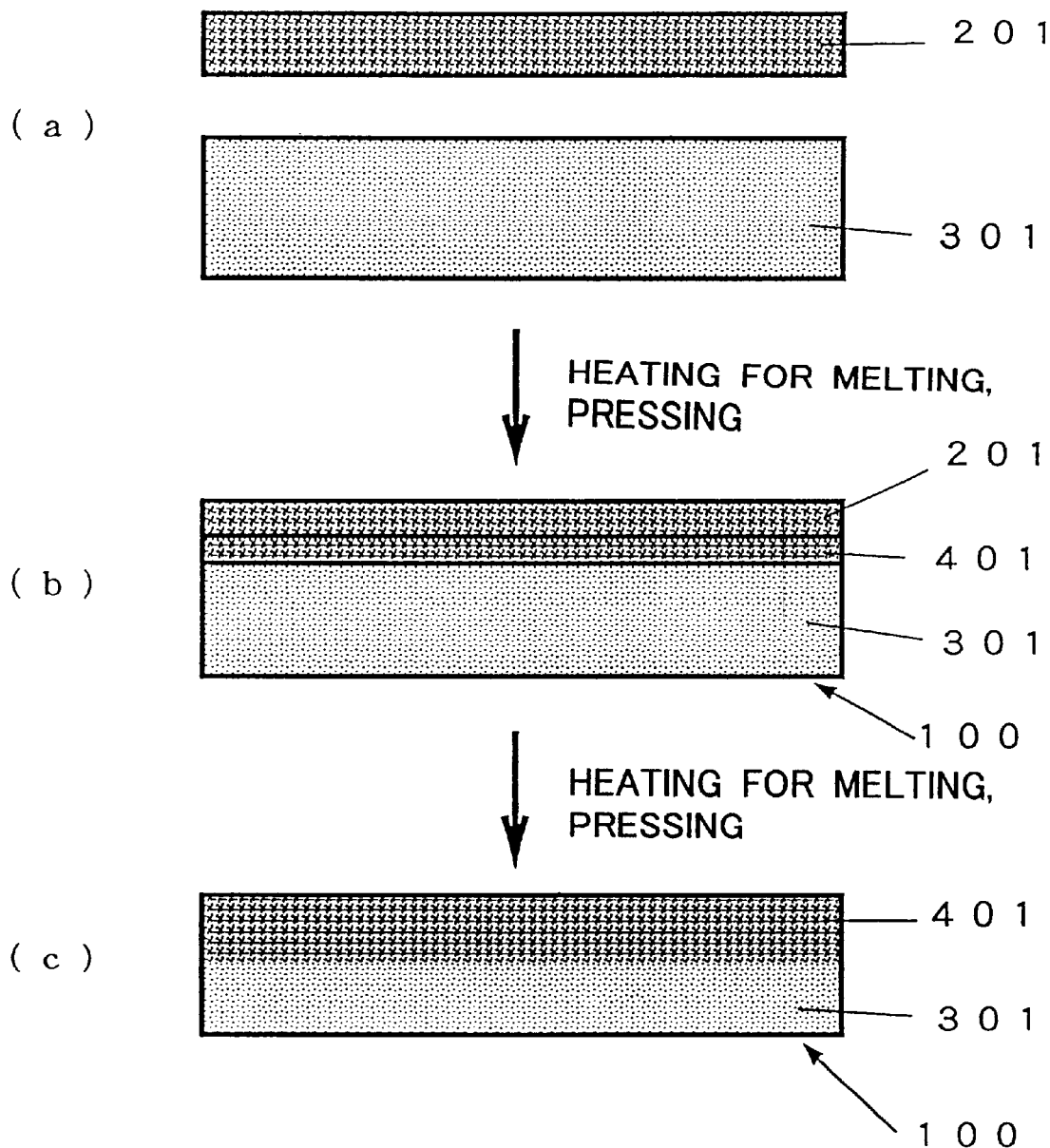
FIG. 1 is a schematic diagram of a process by which a sintered porous composite sheet of the present invention is produced.

FIG. 1 illustrates a sheet manufactured according to a first preferred embodiment. A first porous layer, i.e., an A-component layer 201, and a second porous layer, i.e., a B-component layer 301, are heated under pressure while the first and second layers are laid on top of each other (FIG. 1(*a*)). During heating, the A-component layer melts and infiltrates the B-component layer 301. A three-layered structure of A-A/B-A (FIG. 1(*b*)) is formed. When the melting and infiltrating are further advanced, the structure results in a two-layered structure of A/B-B (FIG. 1(*c*)).

FIG. 2 illustrates a progression of the formation of the layers of the sintered structure. In step (a), an A-component layer and a B-component layer are laid on top of each other, and each has an initial thickness (represented as 100). Then, both are heated while being pressed. The thickness of the A-component layer decreases due to thermal deformation (step (b)), while the thickness of the B-component layer remains substantially the same. When heated further, the A-component layer begins to melt and infiltrate the B-component layer (steps (b) to (d)) while the A-component layer is further pressed. The A-component layer is finally substantially exhausted, and in step (e), an A/B-component layer and a B-component layer are formed.

Examples of changes of the thickness of each component layer at each step are shown in the following Table 2.

TABLE 2

| | | A | B | A + B |
|---|---|---|---|---|
| Step a A, B | Specific Gravity Thickness | 0.07 60 μm | 0.10 100 μm | 160 μm |
| Step b A, B | Thickness | 35 μm | 95 μm | 130 μm |
| Step c A, A/B, B | Thickness | 30 μm | 90 μm | 120 μm |
| Step d A, A/B, B | Thickness | 10 μm | 90 μm | 100 μm |
| Step e A/B, B | Thickness | 0 μm | 90 μm | 90 μm |

In an alternative embodiment, an A-component layer and a B-component layer are laid on top of each other. The A-component layer is then entangled by a needle punch or a high-pressure water stream. A multiple-layered sheet having an (A/B)-B layer structure is formed. The multi-layered sheet is heated and pressed at conditions above the melting point of the A-component to obtain the sintered composite of the present invention. Alternatively, when different fibrous webs are used, a mixed web of A-component and B-component is formed as an A/B-component layer (a first layer). The first layer may be entangled with a B-component layer (a second layer) by a needle punch or a high-pressure water stream so as to obtain a composite sheet having a two-layer structure of (A/B)-B.

Figure 3B:
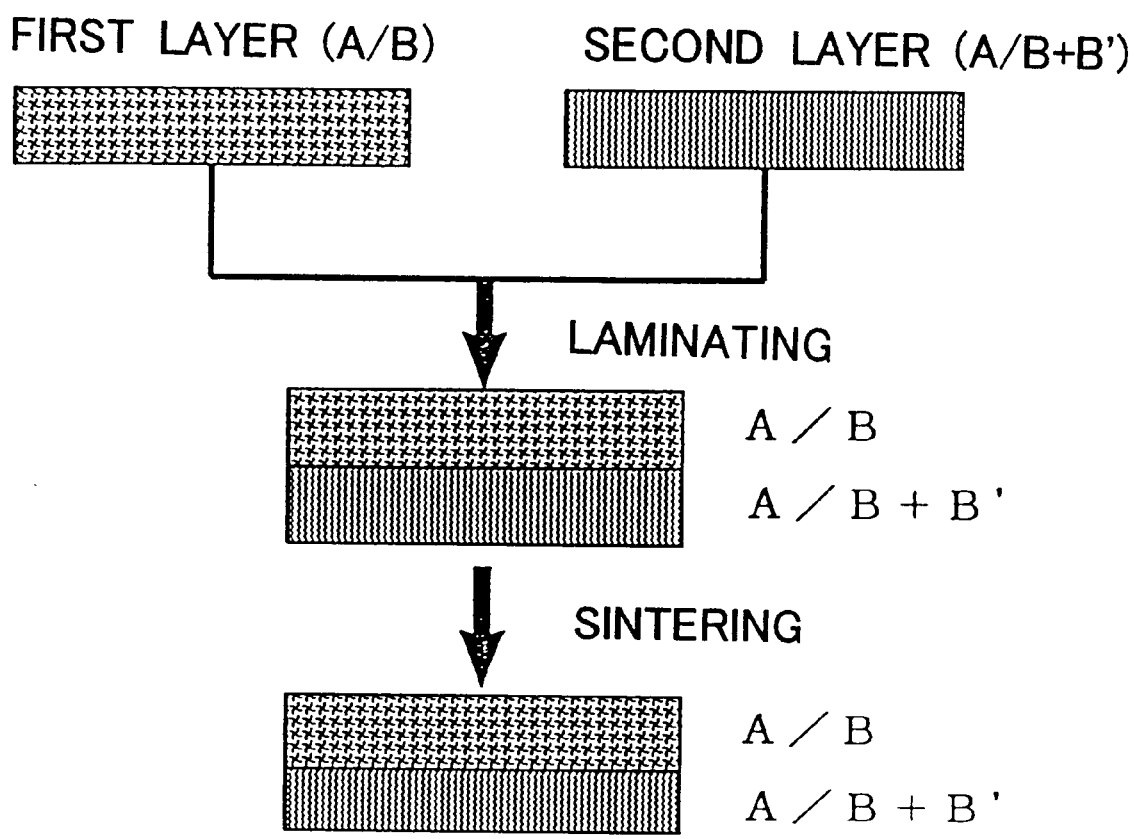
FIG. 3B is a schematic diagram which illustrates a process by which bicomponent fibers are used to produce a sintered porous composite sheet.

A preferred process of forming a sintered structure as explained above is shown in FIG. 3A. The A/B ratio of the first layer is 0.5 or more, and preferably 1.5 to 5.0, while that of the second layer is 1.0 or less, and preferably 0.5 to 0. In order to have the A/B ratio of the first layer sufficiently larger than that of the second layer, the first layer may be heated while the second layer is cooled.

When the A-component layer is rapidly melted, its volume is reduced, creating creases and/or non-homogeneous portions. Generally, it is desirable that the surface be homogeneous. In order to prevent creases, the A-component layer may be pre-thermally compressed and then sintered to the B-component layer.

In an alternative composite sheet, bicomponent fibers comprising a sheath of easily fusible material (A-component) and a core of slightly fusible material (B component) are used. Even if the sheath melts, the core remains substantially solid, so that the contraction which occur with thermal treatment are also decreased, and productivity is improved. Examples of preferred sheath/core embodiments include, but are not limited to:

| Core | Sheath |
|------|--------|
| PET | PE |
| PP | PE |
| PET | Easily Melting PET derivatives |
| PP | EVA |

An example of a sheet employing bicomponent fibers is described below. The first layer is formed from a web comprising a sheath/core fiber of PE/PET, while the second layer is formed from a fibrous web comprising about 50% of PE/PET and about 50% of rayon. The first layer and the second layer are superposed on top of each other, and sintered together at or above the melting point of PE. A sintered composite sheet of the present invention is thus obtained. The first layer preferably contains the A-component in a relatively large amount, and the second layer contains the B-component in a relatively large amount, so that the second layer has a relatively higher thermal stability than the first layer.

Alternatively, another exemplary bicomponent fiber sheet has a spunbond first layer comprising a hydrophobic PE/PET system of about 2 deniers, a mixed web second layer comprising a PE/PET system bicomponent fiber and another fiber(s) in which the bicomponent fiber has a fineness of about 4 deniers, and is preferably treated with a hydrophilicating agent. Both layers are laid on top of each other, and heated and pressed from the side of the first layer. The PE component is shifted from the first layer to the second layer.

The process for forming the sintered structure as described above is shown in FIG. 3B. The composite sheet is preferably water-resistant, but permeable to air and water vapor. Water resistance up to 500 mm $H_2O$ is preferred. Air permeability far exceeds typical air permeable films, and is preferably greater than 100 sec/100 cc. An estimation of the water resistance and the air permeability is carried out according to the following methods:

Water Resistance (mm $H_2O$): JIS L1092 (Low Water-Pressure Method)

Air Permeability (sec/100 cc): JIS 8117P (Gurely Method)

In order to test these properties, a hydrophobic fiber having a mesh as small as possible is employed. Such a web is known as a microfiber-web. The A-component layer has a small mesh, while the B-component layer is highly water repellent.

Such a sintered sheet is an optimum raw material for uses such as an outer or back sheet of sanitary napkins, outdoor sports wear, wrinkle and crease resistant articles and diapers. The porous composite sheet of the present invention has a wide range of applications. For example, the microporous structure according to the preferred embodiments can be used as a biobarrier material, a highly water repellent material, or as an air-permeable material where high sweat absorption is desired.

Figure 4:
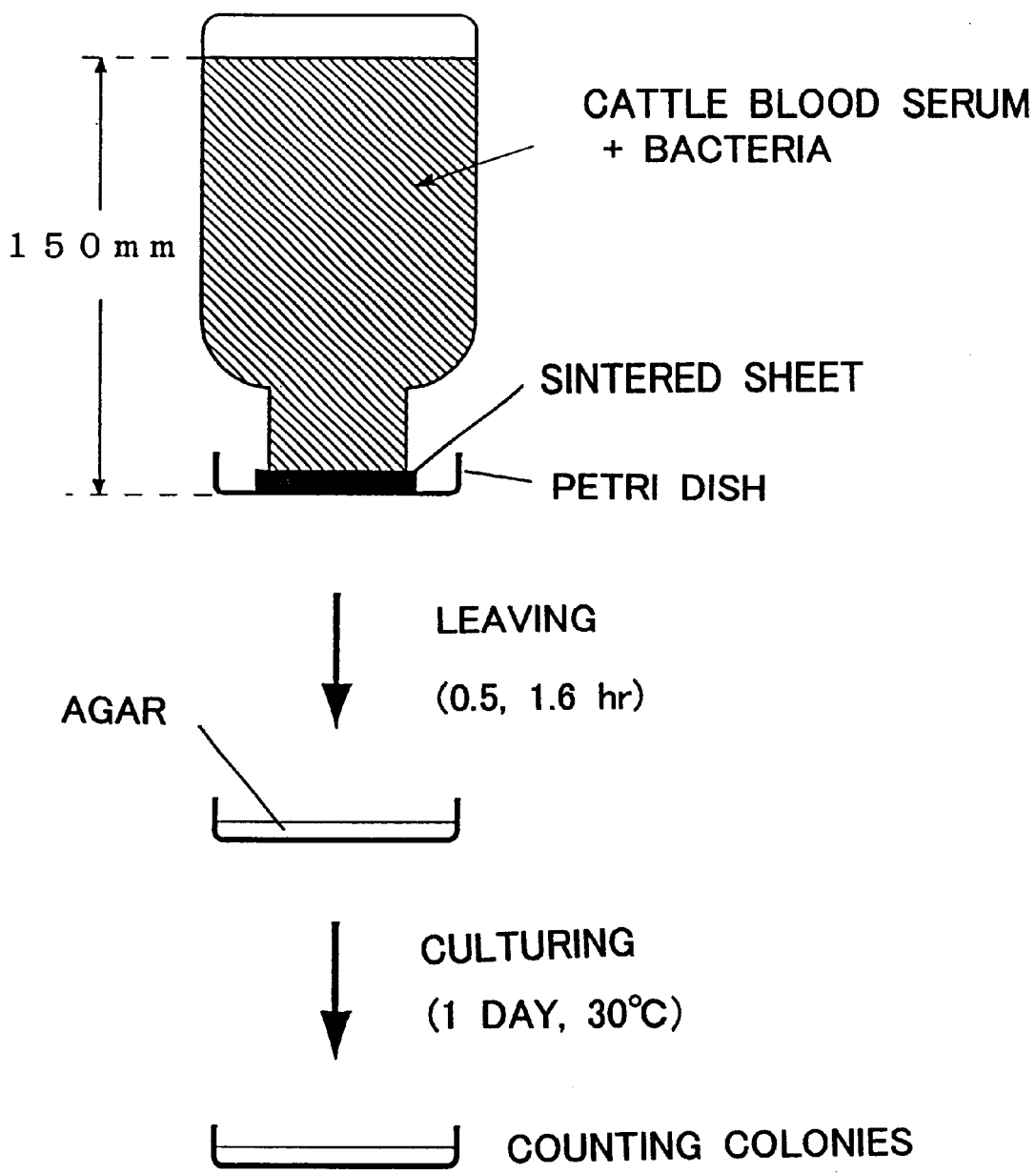
FIG. 4 is a schematic diagram which illustrates a method of testing bio-barrier properties of a sintered porous composite sheet of the present invention.

Biobarrier properties of the sintered porous composite sheet may be confirmed according to a test method shown for example in FIG. 4. First, a test specimen is placed in a glass bottle which contains a bacteria dispersion at a height of 150 mm. A petri dish is placed under the inverted bottle. After 0.5, 1 and 6 hours, the petri dish is removed. An agar is injected into the petri dish and the bacteria cultured at 30° C. for one day, and the colonies counted.

| | |
|---|---|
| Bacteria: | *Serratia Marcescens* IFO 12468 (0.48 μm) |
| | *Pseudomonas Diminuta* IFO 14213 (0.2 μm) |
| Bacteria Dispersion: | 800 ml of Blood Plasma of Cattle which was Diluted with Physiological Brine to three times |

Bacterial Concentration: Approx. $10^6$/ml.

In order to exhibit these biobarrier properties, a repellent microfibril layer is provided as an A-component layer, a hydrophilic cellulose fiber is provided as a B-component layer, and both layers are sintered together to form an A-(A/B)-B layer structure. Such a sintered porous composite sheet may be used in surgical or medical applications such as a surgical gown, a surgical drape and a mask. The sheet may also be used as a vacuum cleaner filter. Alternatively, the composite sheet may be utilized as the surface sheet of an absorbent product.

Important indicators for testing the effectiveness of absorbent products are absorbing speed and wet-back. Conventionally, it was thought that a very thick structure was necessary to effect one-way (wet-back) water absorbing properties. However, by using the sintered structure of the present invention, a one-way water-absorptive sheet which is highly water absorbent is realized; i.e., wet-back is substantially reduced.

One exemplary sheet for realizing this objective comprises a hydrophobic easily fusible web such as PP or PE as an A-component layer and a hydrophilic cellulose porous sheet as a B-component layer. The A-component layer is melted and infiltrates the B-component layer. Both layers are thus sintered together until the A-component is nearly completely adhered to the B-component layer to form the (A/B)-B-component layer.

More particularly, a thin sheet of low denier and specific weight of about 20 g/m$^2$ or less is desired as an A-component layer. For example, a spunbond comprising a bicomponent fiber of PP as a core and PE as a sheath may be employed. These sheets are drawn in both the cross direction and the machine direction to form thin, soft sheets having a very high fitness. The B-component layer preferably comprises TCF, a cellulose nonwoven fabric such as Wenliese, tissue paper, an air-laid mat of wood pulp, a synthetic fiber web treated to be hydrophilic, or a sheet-like material having high water absorbency.

FIG. 5 shows the effects that sintering has upon water-drop D placed upon an A-component layer 202. In FIG. 5(a), the water-drop D is placed upon an A-component layer 202 comprising an aggregate of fine fibers. There, the water-drop D shows little permeability to the A-component layer 202. FIG. 5(b) shows that when a B-component layer 302 is laid on top of the A-component layer 202, there are substantially no changes of the water-drop D. However, when the A-component layer is sintered to the B-component layer to form a sintered portion 402 as shown in FIG. 5(c), the water-drop D begins to permeate the surface of the A-component layer 202. When the sintering is increased so that almost all of the A-component layer infiltrates the B-component layer 302, a remarkably higher permeability is revealed.

The porous composite sheet as shown in FIG. 5(d) appears as a thin film having a smooth, fuzz-less surface. The hydrophilic component on the surface comprises a plurality of pores on the surface. The sheet rapidly absorbs and transfers water to the B-component layer 302. Due to smoothness of the surface, minute water drops are substantially entirely absorbed without wiping. These sheets may be readily applied to the following applications:

(1) blood-absorbing sheet materials:
  surgical tray, tray for removing drainage from raw meat; and
  absorptive-plug coating-material (for ophthalmology, or for cerebral surgery)
(2) sanitary material:
  diffusion sheet or surface material of a physiological article;
  surface cover material of a tampon; and
  diffusion sheet or top sheet of a diaper.
(3) lint-free wipes.

The sheets of the foregoing embodiments have been sintered over their entire surface. However, partially sintered porous composite sheets also have a broad range of uses. For instance, a sheet having a first hydrophobic porous layer partially bonded to a second high water absorbing porous layer have excellent absorbency properties, fit and feel.

FIG. 6 illustrates three preferred sintered sheets. FIG. 6(a) illustrates a porous composite sheet 100 which as been sintered along substantially all of its surface. Alternatively, FIG. 6(b) illustrates a porous composite sheet 100 having sintering 403 restricted to the center area of the sheet. Still further yet, FIG. 6(c) illustrates a porous composite sheet 100 having a plurality of discrete sintered areas 403.

Figure 7:
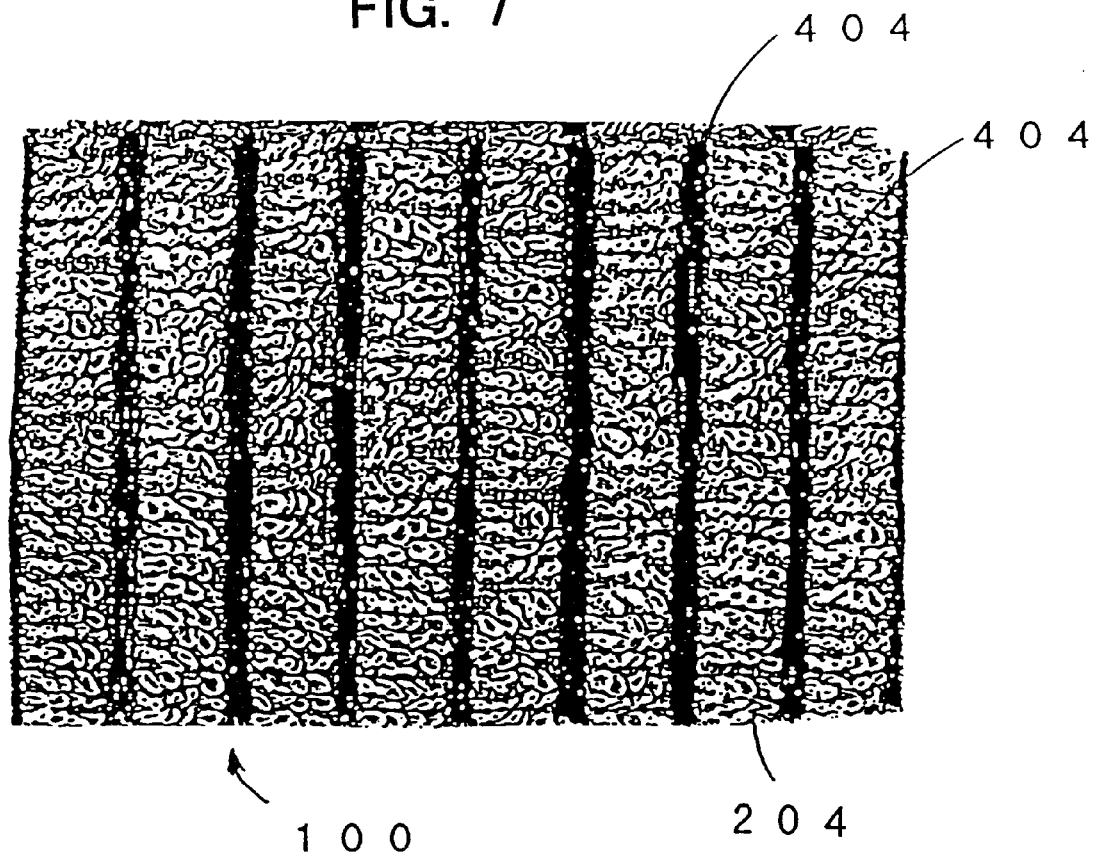
FIG. 7 is a plan view which illustrates the sintered porous composite sheet of a second preferred embodiment of the present invention.
Figure 8:
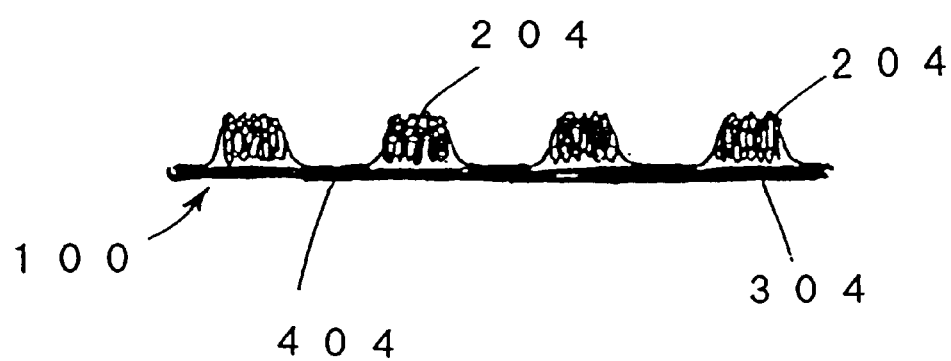
FIG. 8 is a partial longitudinal sectional view of the sheet of FIG. 7.
Figure 9:
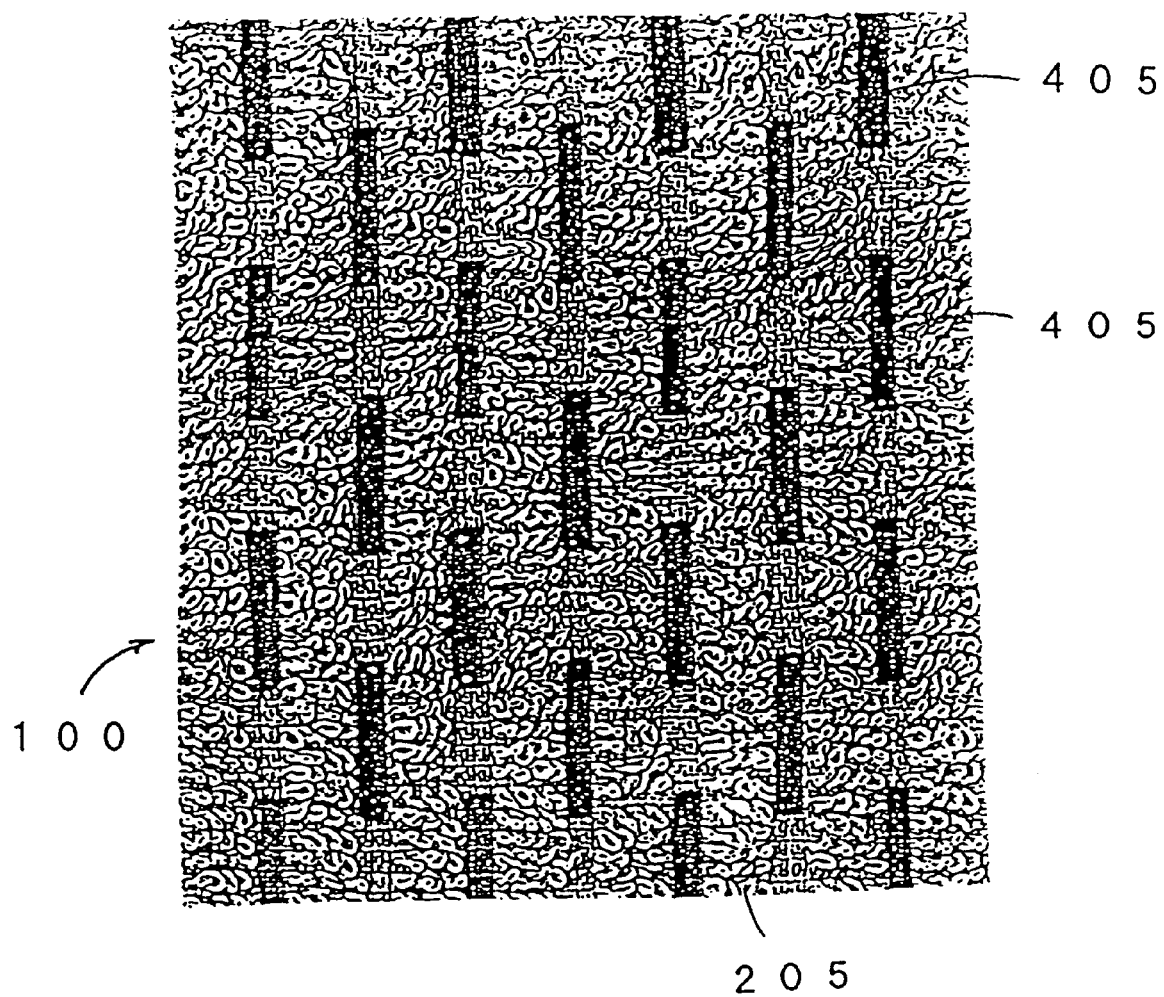
FIG. 9 is a plan view which illustrates the sintered porous composite sheet of a third preferred embodiment of the present invention.
Figure 10:
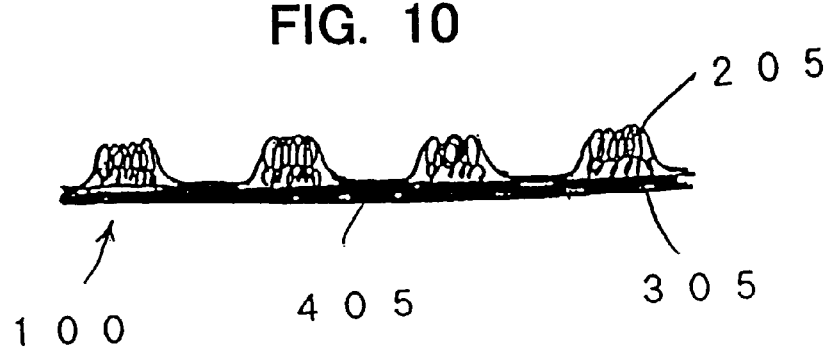
FIG. 10 is a partial longitudinal sectional view of the sheet of FIG. 9.
Figure 11:
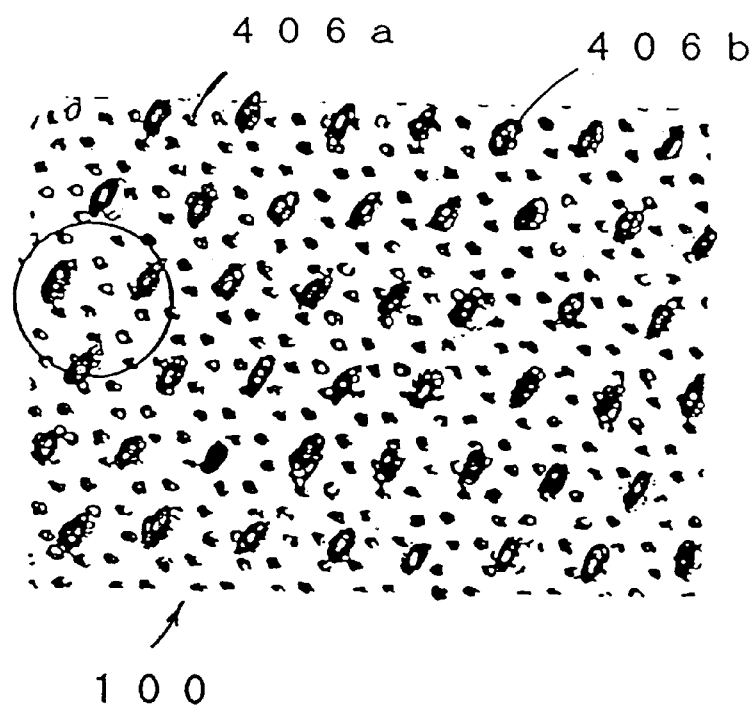
FIG. 11 is a plan view which illustrates the sintered porous composite sheet of a fourth preferred embodiment of the present invention.
Figure 12:
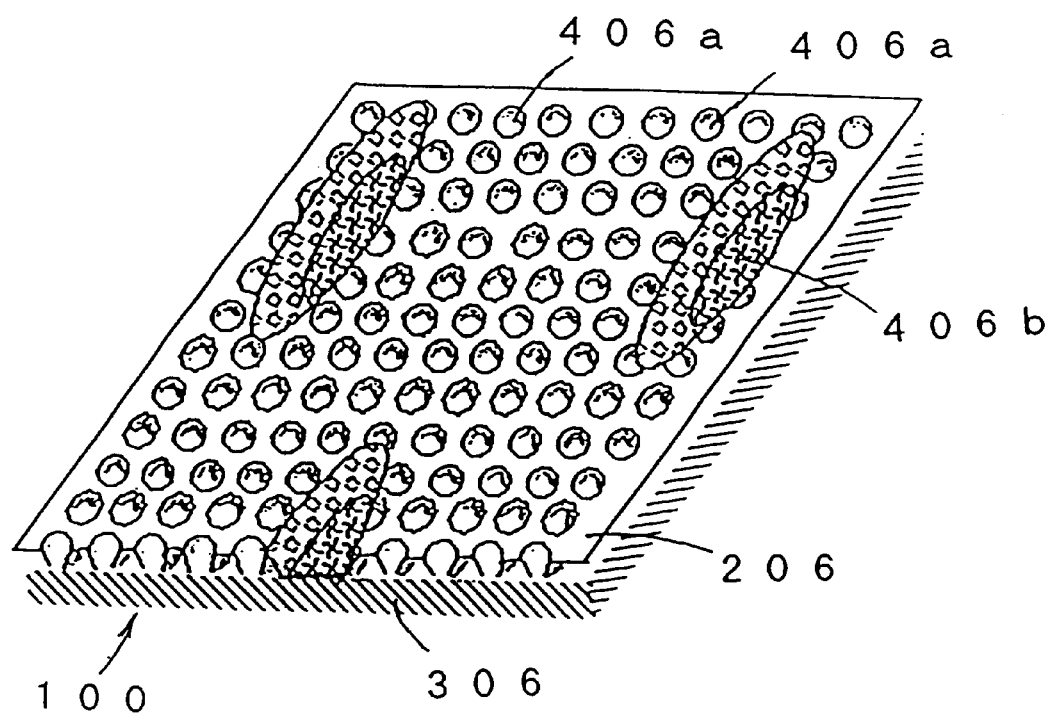
FIG. 12 is an enlarged perspective view of FIG. 11.

FIGS. 7 and 8 illustrate sheets wherein the sintered areas 404 are configured as a plurality of parallel lines binding the A-component layer 204 and the B-component layer 304. FIGS. 9 and 10 illustrate sheets wherein sintered areas 405 are configured as a plurality of parallel, discontinuous lines binding the A-component layer 205 and the B-component layer 305. Alternatively, FIGS. 11 and 12 illustrate sheets having a plurality of small sintered areas 406a in the form of dots. In addition, the sheet has sintered areas 406b each of which is larger than each of the small sintered areas 406a. Areas 406b are preferably shaped substantially as ellipses. The sintered porous composite sheets of FIGS. 7–12 have partially sintered areas arranged according to a predetermined distribution. This arrangement facilitates the absorption of moisture at the sintered areas, while the hydrophobic property of the first porous layer at the non-sintered areas shuts out moisture to maintain a dry sheet.

Figure 13:
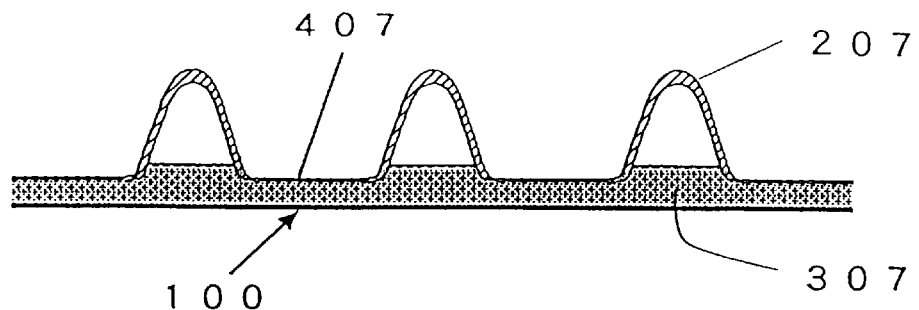
FIG. 13 is a longitudinal sectional view of the sheet according to a fifth preferred embodiment of the present invention.
Figure 14:
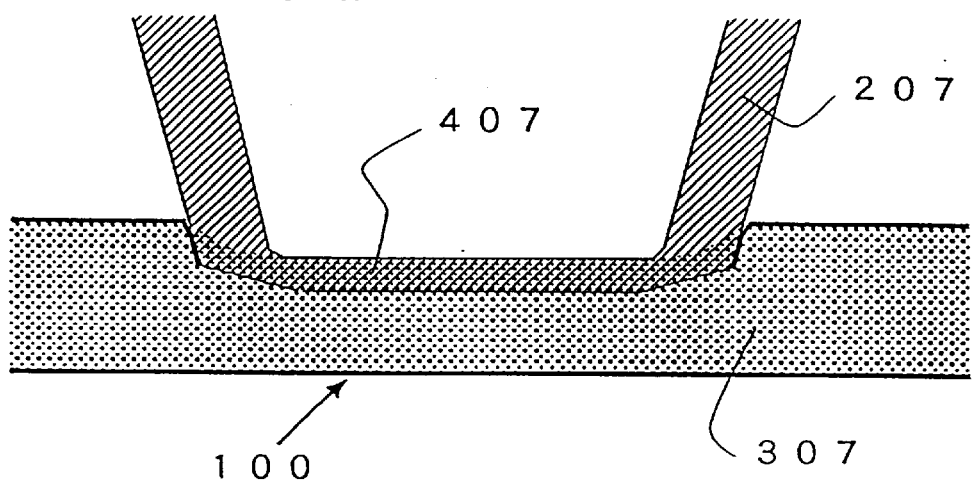
FIG. 14 is an enlarged perspective view of FIG. 13.

When the sintered areas and the non-sintered areas are arranged three-dimensionally, the absorbency characteristics further improve. FIGS. 13 and 14 illustrate a sintered porous composite sheet 100 having a first wave-shaped porous layer 207 positioned on a second flat porous layer 307. Both layers are sintered together at trough areas 407 of the first porous layer 207. One of the uses for a sintered porous composite sheet as shown in FIGS. 13 and 14 is a top sheet for an absorbent product. The strong hydrophobicity of the first porous layer 207 keeps the crests which contact the skin dry, while the trough areas tend to have a large water permeability because the first hydrophobic porous layer 207 is sintered and united with the second hydrophilic porous layer 307 containing a cellulose material as shown in FIG. 14. Therefore, liquid which is gathered in the trough is readily absorbed into the second porous layer 307 without rewetting.

Figure 15:
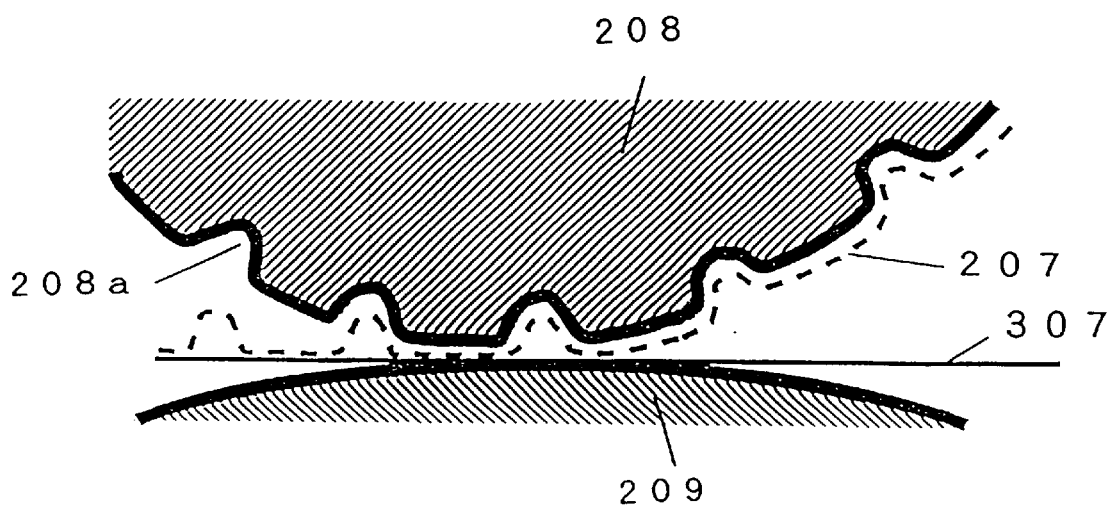
FIG. 15 is a sectional view of the apparatus for producing a sintered porous composite sheet as shown in FIG. 14.

A sintered porous composite sheet having such a structure can be manufactured according to various methods. For example, as shown in FIG. 15, the first porous layer 207 is attached to a roll 208. A channel 411a is formed on the periphery of roll 208. Channels 411a have suction means formed therein to deform layer 207 into a wave-shape. A second flat porous layer 307 is laid on top of the first layer. Thereafter, both layers are sintered at the trough areas of the first porous layer, so that a sintered porous composite sheet 100 as shown in FIG. 13 is formed.

Figure 16:
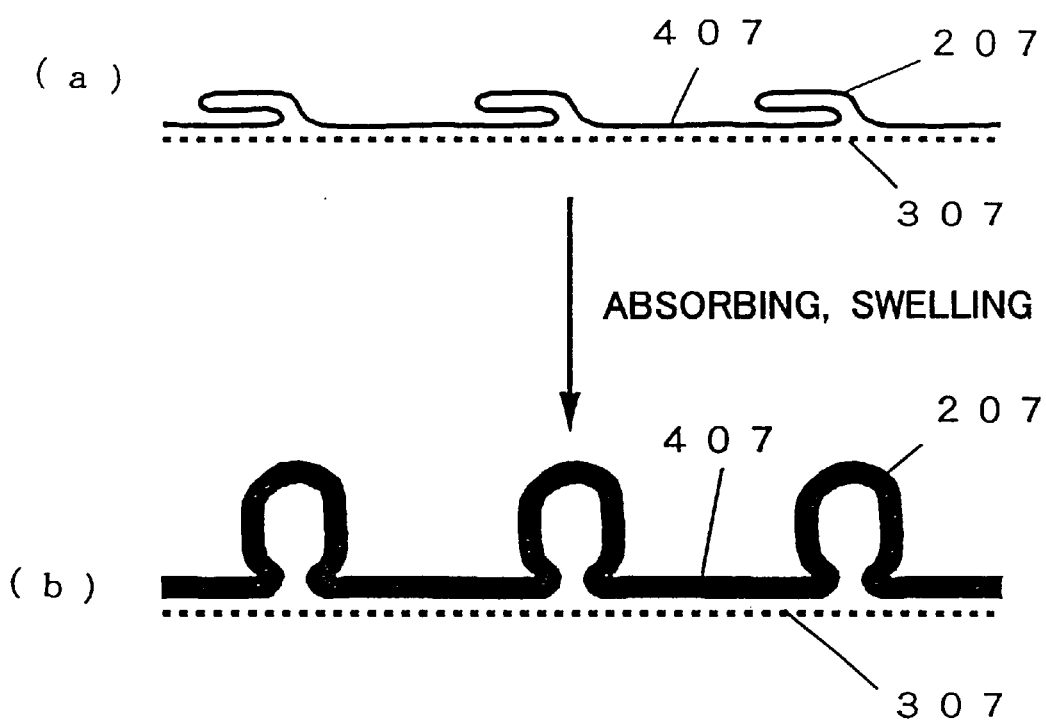
FIG. 16 is a schematic diagram of a sintered porous composite sheet of FIG. 13 before and after liquid absorption.

In a sheet-like composite absorbent as shown in FIG. 13, liquid provided on the first porous layer 207 is readily absorbed at sintered areas 407 formed in the trough areas, and is fixed at the non-sintered areas in the second porous layer 307. As shown in FIG. 16(a), the A-component 207 lays substantially flat when no liquid is absorbed by the second porous layer 307. However, as liquid is absorbed, as shown in FIG. 16(b), the crest areas of the non-sintered areas of the first porous layer 207 stand erect. Consequently, the wet areas which touch the skin are substantially decreased, leaving improved feeling and separating the skin from moisture.

Figure 17:
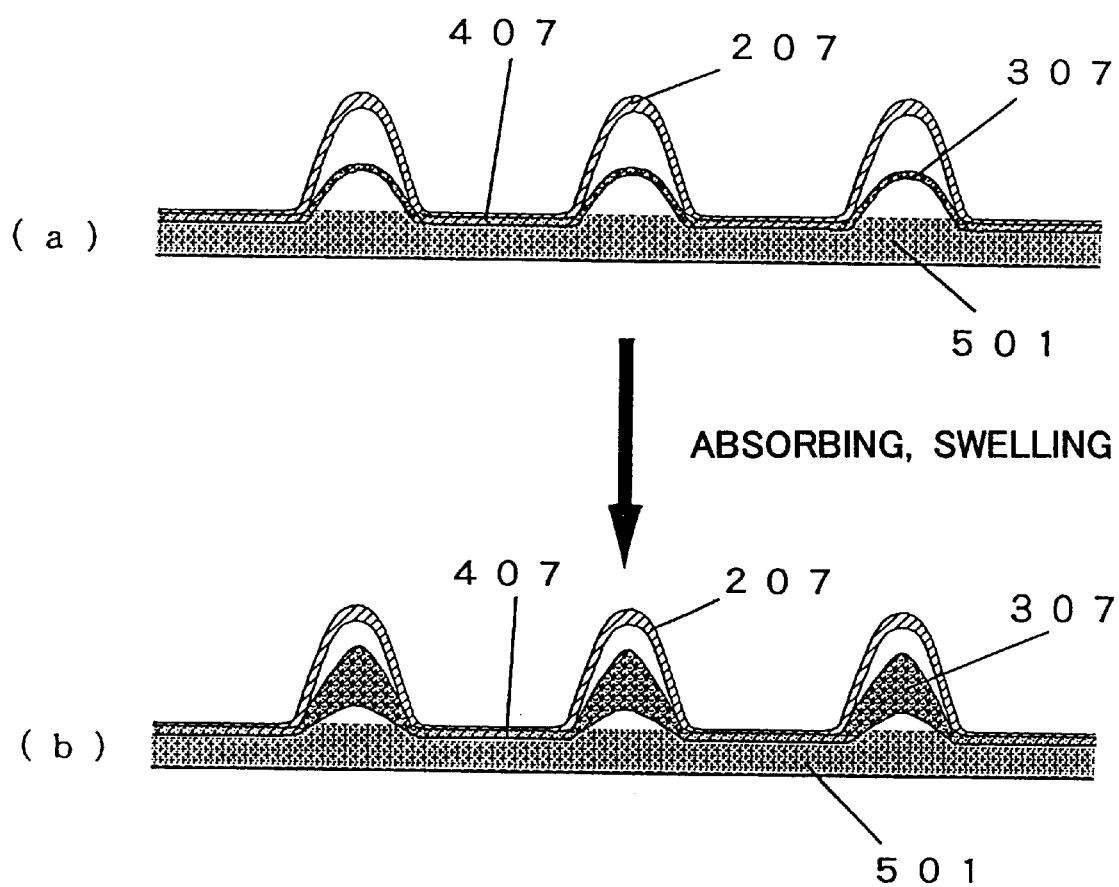
FIG. 17 is a longitudinal sectional view of the sheet of a sixth preferred embodiment of the present invention.

As seen in FIG. 17, the sintered porous composite sheet of FIG. 13 may be placed on top of a liquid-permeable sheet 501. The first porous layer 207 acts as a top sheet, the second porous layer 307 as an absorbent body and the liquid-permeable sheet 501 as a back sheet. In the sheet-like composite of FIG. 17, swelling occurs when water is absorbed, since the thickness of the porous second layer 307 increases with absorption of liquid as shown in FIG. 16(b).

As shown in FIG. 18(a), belt-like or string-like polymeric absorbent 502 may be positioned within each of the spaces formed by the first porous layer 207. This type of composite sheet finds application where a larger absorbing capacity is required. The swollen polymeric absorbent 502 is illustrated in FIG. 18(b).

Figure 18:
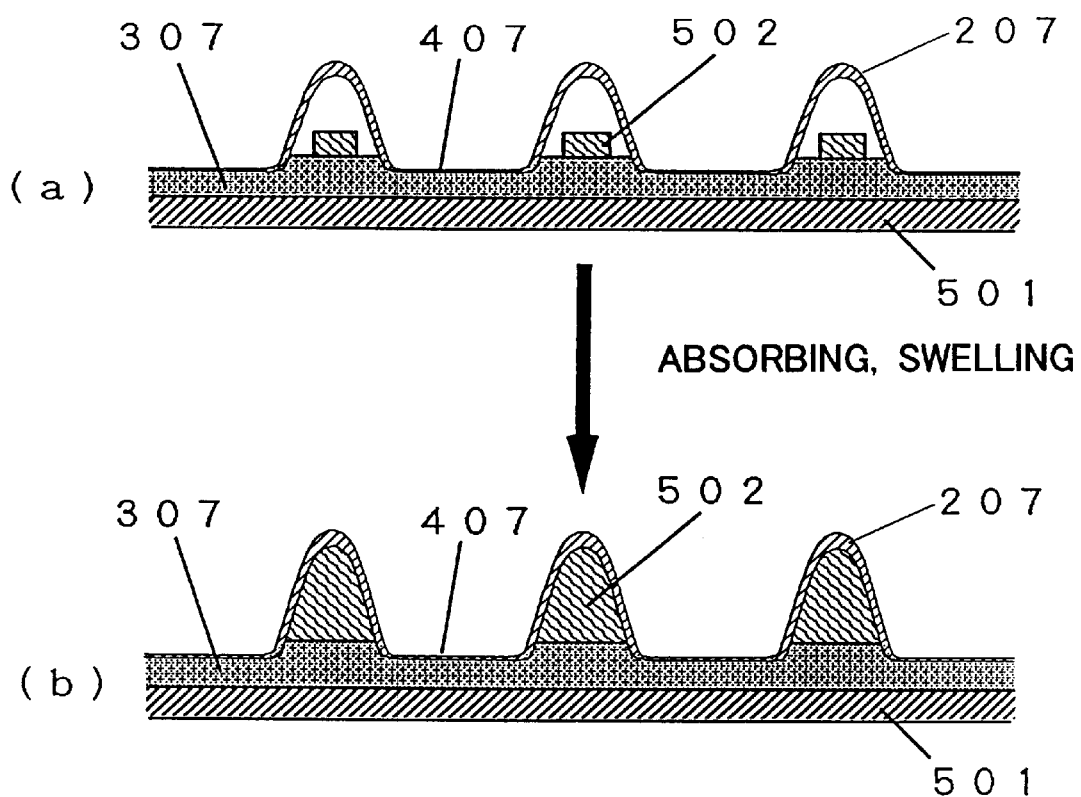
FIG. 18 is a longitudinal sectional view of the sheet of a seventh preferred embodiment of the present invention.
Figure 19:
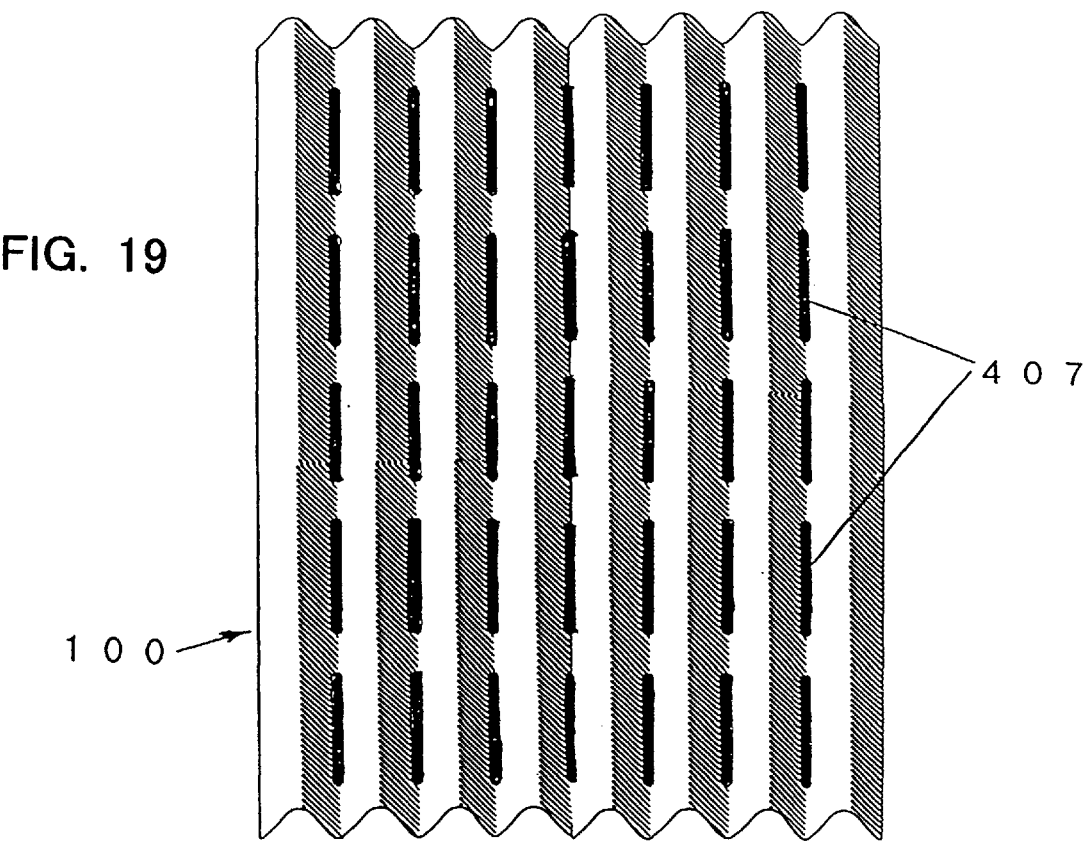
FIG. 19 is a plan view of a sheet of an eighth preferred embodiment of the present invention.
Figure 20:
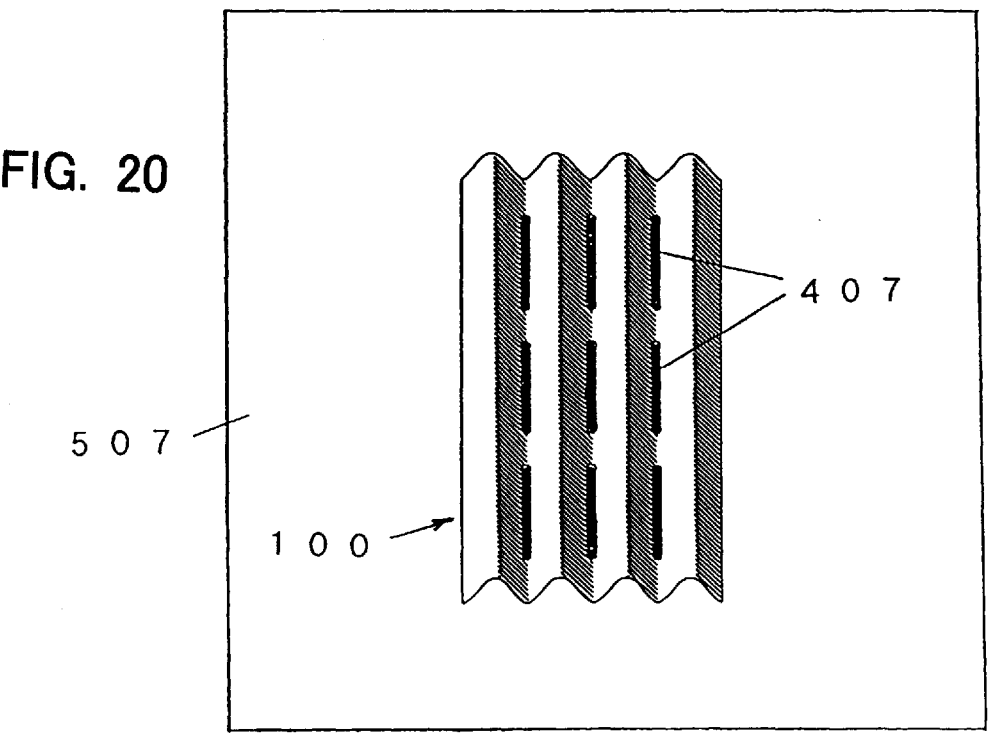
FIG. 20 is a plan view of a sheet of a ninth preferred embodiment of the present invention.
Figure 21:
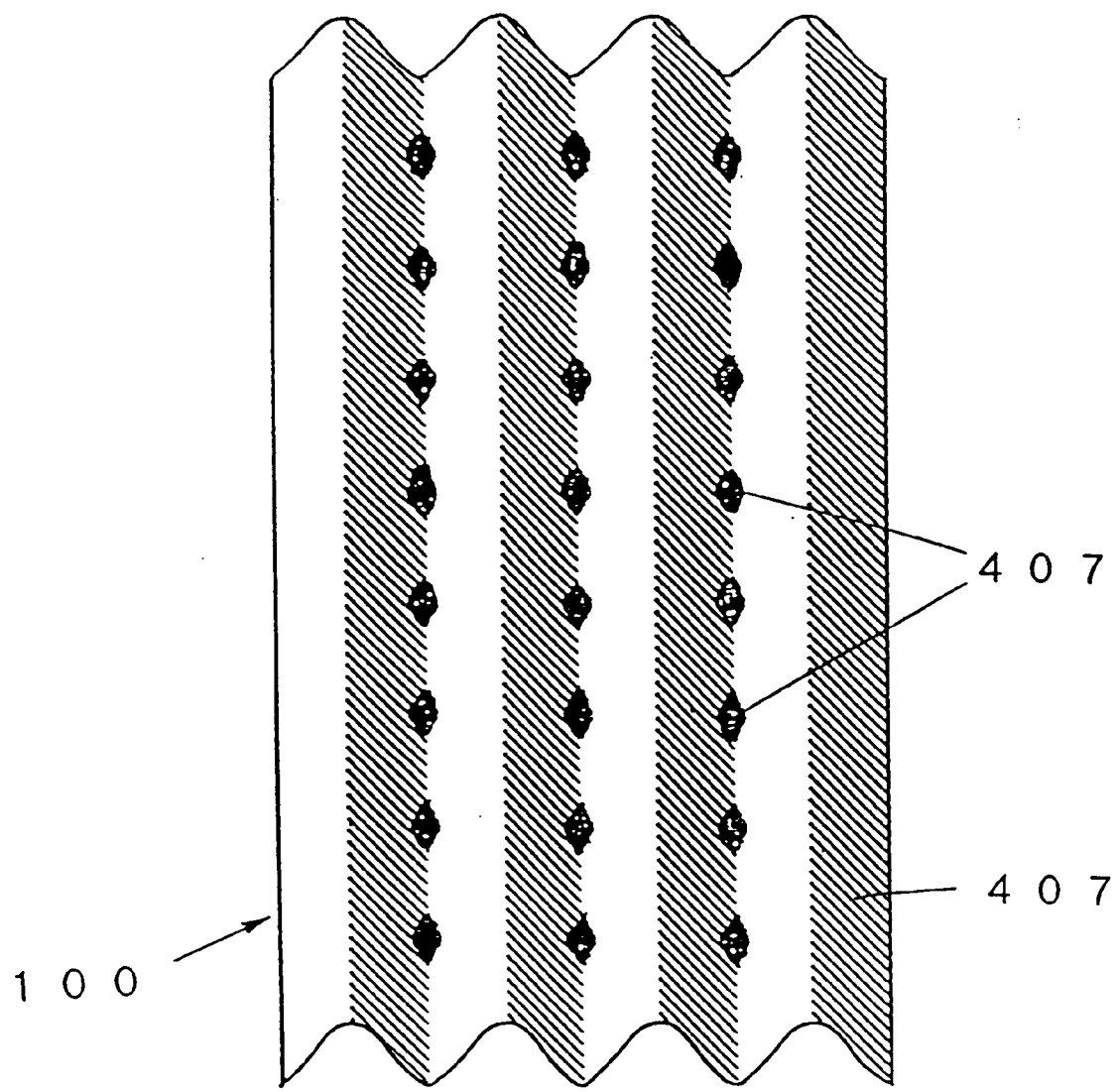
FIG. 21 is a plan view of a sheet of a tenth preferred embodiment of the present invention.

In FIGS. 13, 17 and 18, the sintered area 407 may be a continuous line extending along the longitudinal direction of the trough areas, or a plurality of short lines disposed in a line as shown in FIG. 19. The sintered porous composite sheet 100 can be smaller than the absorbent material and cover part of the sheet-like absorbent 503 to form a sheet-like composite absorbent body. The sintered areas 407 may optionally approximate a plurality of aligned round dots. If necessary, it is possible to size the openings of the sintered areas to allow a predetermined amount of liquid to pass through the sintered areas. FIGS. 20–21 represent further preferred sintering arrangements for the porous composite sheet.

Figure 22:
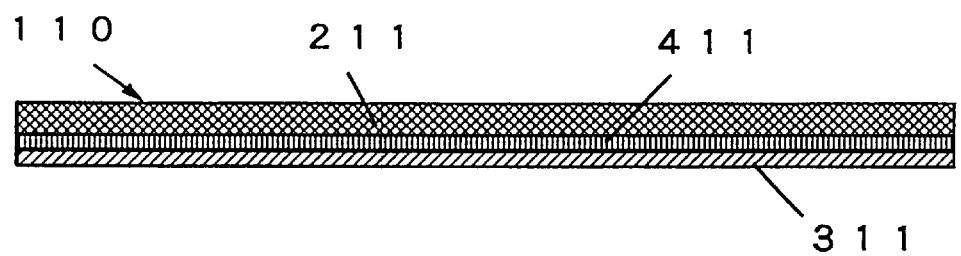
FIG. 22 is a longitudinal sectional view of the water-permeable composite sheet of FIG. 11.

Another preferred embodiment for the porous composite sheet having a hydrophilic surface is shown in FIG. 22. The first layer 211 comprises a hydrophobic material and the second porous layer 311 comprises a hydrophilic material. Layers 211, 311 are laid on and sintered together to form a water permeable composite sheet 110 having an A/B-component layer 411 therebetween.

Figure 23:
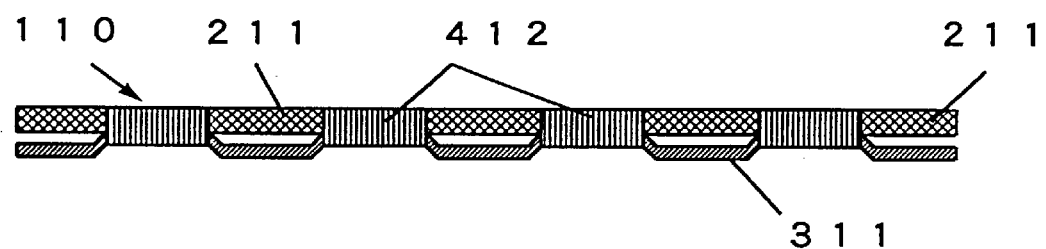
FIG. 23 is a longitudinal sectional view of the water-permeable composite sheet of FIG. 12.
Figure 24:
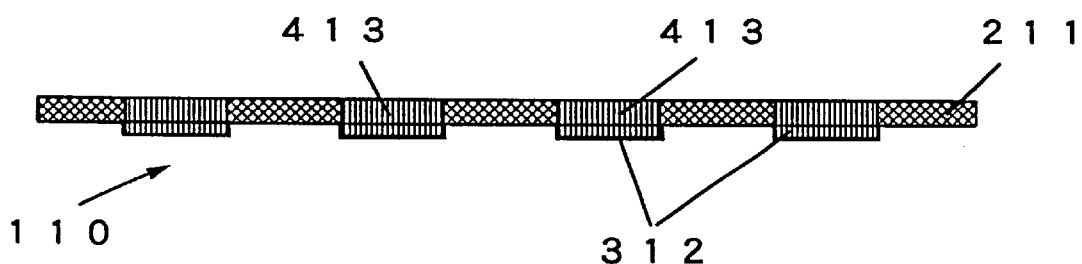
FIG. 24 is a longitudinal sectional view of the water-permeable composite sheet of FIG. 13.

FIG. 23 shows another preferred water permeable composite sheet 110 having areas where first hydrophobic porous layer 211 and second porous layer 311 are unsintered, and areas where A/B-component layers 412 are sintered. FIG. 24 shows another preferred water permeable composite sheet 110. First porous layer 211 and A/B-component layers 413 alternate. A plurality of second layers 312 are arranged on first layer 211.

Figure 25:
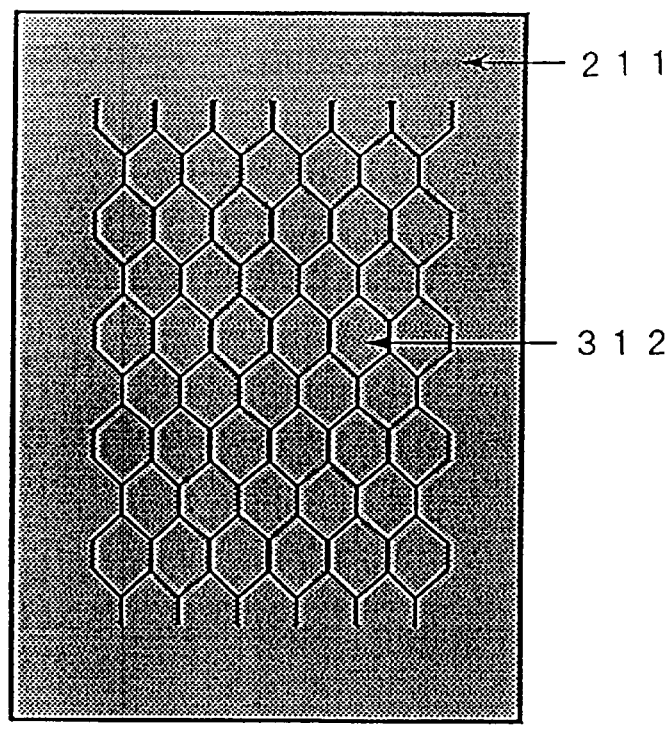
FIG. 25 is a longitudinal sectional view of the water-permeable composite sheet of FIG. 14.
Figure 26:
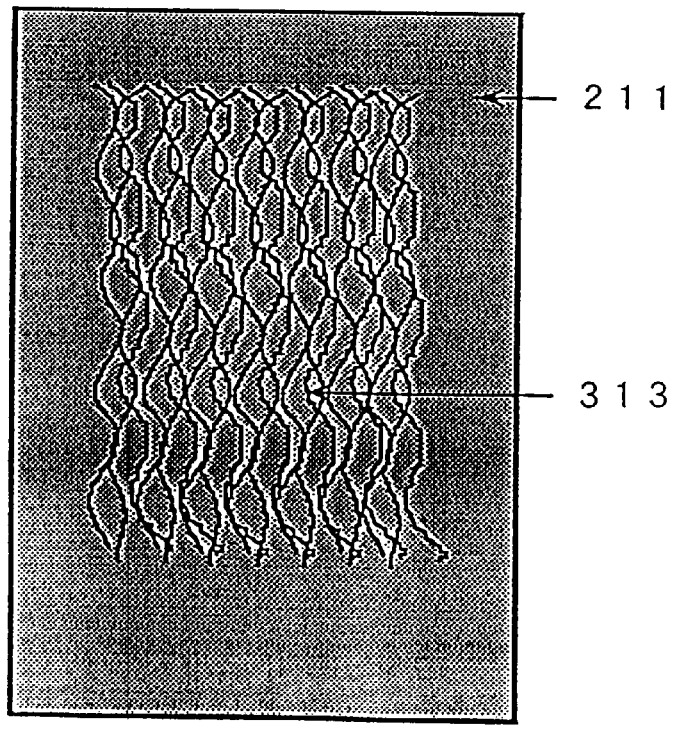
FIG. 26 is a longitudinal sectional view of the water-permeable composite sheet of FIG. 15.

FIG. 25 illustrates another preferred water-permeable composite sheet 110. A first hydrophobic layer 211, e.g., PE/PET, has bicomponent spun-bond nonwoven fabric laid thereover. A net of extruded hydrophobic is placed between the sheets which are then sintered together. FIG. 26 shows a water-permeable composite sheet 110 using, in place of the PE net of FIG. 25, a PP foam 313 which is hydrophilicated and stretched in the width direction as a second layer. When the B-component layer of the net is hydrophilicated at its surface, water permeable regions are formed along the second layer.

In general, the higher the applied temperature to the sintered portions, the larger the water permeability at the sintered portion. In addition, the surface becomes harder and film-like and the surface strength increases. On the other hand, when the temperature and pressure are low, the surface texture is kept soft, but water permeability decreases. The same materials will thus provide composite sheets having different properties by adjusting the temperature and pressure applied. Thus, it is possible to obtain water permeable composite sheets having predetermined properties by choosing the manufacturing parameters.

Hereinafter, working examples of the present invention will be explained.

EXAMPLES

EXAPLE 1

Combination of First Hydrophobic Layer and Second Layer

Preparation of A-Component Layer and B-Component Layer

The A-component layer comprises a PE meltblown nonwoven fabric having a thickness of about 1 mm (which has a specific weight of about 15 g/m$^2$, and a specific gravity of about 0.02 g/m$^3$.). The B-component layer comprises a spunlace nonwoven having a thickness of about 1 mm and was prepared by entangling 1.5 d×35 mm of polyester with a high pressure water stream. The B-component layer has a specific weight of about 50 g/m$^2$, and a specific gravity of about 0.05 g/m$^3$.

Conjugation and Sintering of A-Component Layer and B-Component Layer

A B-component layer was laid on top of the A-component layer resulting in a thickness of about 2.5 mm. Silicone paper was placed on the A-component layer. The layers were then heated at a temperature of 160° C. under a pressure of 5 kg/cm$^2$ for a period of about one minute using a press having a hot plate thereon. As a result, the surface was compressed to about 0.8 mm.

Characteristics of Sintering Treated Articles

Water resistance was tested while the A-component layer and the B-component layer were laid on top of each other according to JIS 1092 (Low Water-Pressure Method). Water resistance was found to be about zero. On the other hand, the sintered product exhibited a water resistance of 100 mm H$_2$O, and a specific gravity of 0.8 g/cm$^3$.

EXAPLE 2

Combination of First Hydrophobic Layer and Second Layer

Preparation of A-Component Layer and B-Component Layer

The A-component layer comprises a spotbond nonwoven fabric having a specific weight of about 20 g/m$^2$, which comprises PP-fibers (1.5 d×35 mm) and has a specific gravity of about 0.6 g/m$^3$. The B-component layer comprises a sliced sheet of a polyester hardened polyurethane foam having continuous foaming properties. The B-component layer has an apparent specific gravity of about 0.03 g/m$^2$, a thickness of about 3 mm and a water-drop surface tension of about 75° C.

Conjugation and Pre-hotpress of A-Component Layer and B-Component Layer

The heating and pressing apparatus comprises a pair of rolls. The upper roll has a diameter of about 300 mm, and is provided with a heating apparatus and solvent. The surface of the upper roll is preferably chrome-plated and satin-finished. The lower roll has a diameter of about 400 mm, is chrome-plated, and is unheated. Silicone separating-paper is placed on the A-component layer and a B-component layer is laid on top of the A-component layer. The layers were then continuously pressed at a surface temperature of about 160° C. at a rate of about 3 m/min. at a pressure of about 5 kg/cm$^2$. The heated roll was applied to the A-component layer. As a result, a nonwoven fabric having the B-component was sintered on the surface of the urethane of the A-component. The water-pressure resistance of the resulting sheet was about 20 mm H$_2$O or less.

Sintering Treatment

The above sheet was again passed between the rolls at a surface temperature of about 200° C. at a rate of about 1 m/min. at a pressure of about 15 kg/cm$^2$, to obtain a sheet having a thickness of about 0.5 mm, whose surface was in the form of a smooth synthetic leather. The water-pressure resistance of this sheet was increased to 300 mm H$_2$O, at a contact angle of about 90° was shown.

EXAPLE 3

Sintered Sheet Combined with Cellulose Sheet

Preparation of A-Component Layer and B-Component Layer

An A-component layer comprising a spunbond nonwoven fabric (having a trade name "ELVES" made by UNICHIKA, and a specific weight of 25 kg/m$^2$) was prepared. The nonwoven fabric comprises filaments of a bicomponent fiber of a polyester core and polyethylene sheath. The B-component layer comprises a sheet of airlaid-pulp nonwoven fabric (trade name "QUINOCLOTH" made by HONSHU SEISHI, and a specific weight of about 120 g/m$^2$). A polyacrylic polymer absorbent (trademark "IM-3000" made by SANYOKASEI) is contained within the B-component layer at about 50 g/m$^2$.

Conjugation and Sintering of A-Component Layer and B-Component Layer

The A-component layer was laid on the B-component layer, resulting in a thickness of about 3 mm. A silicone separating-paper was placed on the A-component layer. The A-component layer, the B-component layer and the separating-paper were heated from the side of the A-component layer to a temperature of about 180° C. with pressure applied. The resulting sheet had a thickness of about 1 mm.

Water-Absorbing Property of Sintered Article

The sintered sheet was very water absorbent. Little liquid was left after absorbing water. The following characteristics were observed:

| | |
|---|---|
| • water-absorbing speed | 2 sec./100 cc |
| • Rewet | 0.1 g or less |

Application to Tray for Raw Meat

Two beef steaks were packed in a polystyrene tray. The steaks were somewhat blood-stained on the underside thereof. The sintered sheet was spread in one tray, while a QUINOCLOTH was spread in the other tray. The trays were wrapped and placed in a refrigerator for 24 hours, and thereafter, compared with each other. In the case of the sintered sheet, there was little difference in color between the upper surface and the contact surface thereof, but in the case of the QUINOCLOTH, some discoloration was observed. Furthermore, with the QUINOCLOTH, blood adhered between the meat and the sheet. In the sintered sheet, no such blood was observed.

EXAPLE 4

Stretched Sintered Body

Preparation of A-Component Layer and B-Component Layer

The A-component layer comprises a meltblown elastic nonwoven fabric having a specific weight of about 40 g/m$^2$ and having about 70 parts of SEBS (trademark "CRAYTON RESIN") and about 30 parts of EVA (trademark "EVAFLEX"). The web had a specific gravity of about 0.05 g/cm$^3$. The B-component layer comprises a spunlace nonwoven fabric (specific weight of about 30 g/m$^2$). The B-component layer was prepared by treating a parallel-carded web with high-pressure water. The parallel-carded web comprised about 40 parts polyester fiber (1.2 d×35 mm), and about 60 parts bicomponent fiber (trademark "NSF-PT" made by DAIWA BOSEKI; 1.5 d×35 mm) of polymethylenepenthane sheath, and PP core. The B-component layer nonwoven fabric had a specific gravity of about 0.08 g/cm$^3$. The nonwoven fabric of the B-component layer was elongated about 20% in a cross direction (CD).

Conjugation and Sintering the A-Component Layer and B-Component Layer

The B-component layer was laid on top of the A-component layer, and both layers were pre-pressed at about 5 kg/cm$^2$ using a mangle at room temperature. Even by applying cold pressure, a temporary conjugation was obtained.

The A-component layer and the B-component layer were then passed between a pair of heating rolls with the B-component layer on top. The surface of the upper roll of the heating rolls was chrome-plated, and had been heated to about 120° C. The lower roll was made from silicone rubber, and was not heated, but maintained a temperature of about 70° C. from residual heat of the upper roll. The conjugated body was pressed at a pressure of about 10 kg/cm$^2$ at about 3 m/min. This process transformed the A-component layer into a pliant sheet having an opal-like color. The resulting composite sheet exhibited excellent stretching properties. After drawing the sheet by about 150%, it had an elastic recovery factor of 85%. The resulting sintered porous composite sheet had the following physical properties.

| | |
|---|---|
| Apparent Specific Gravity | 0.12 g/cm$^3$ |
| Air-Permeability | 30 sec/100 cc |
| (JIS P8117 Gurley Method) | |
| Water Resistance | 400 mm H$_2$O |
| (JIS L1092 Low Water-Pressure Method) | |

Application of Sintered Articles to Diaper

The above sintered porous composite sheet is particularly adaptable for use as a back sheet for disposable diapers or training pants for children. Commercial training pants having a PE air-permeable back sheet film were modified so that a portion of the back sheet was replaced with a sintered sheet. Comparative tests were performed. No significant differences between the sintered and PE sheet with respect to leakage were observed. The smoothness, comfort and fit of the sintered sheet was particularly apparent over the PE sheet.

Application to Operative Gloves or Cap in Which Bio-barrier Properties Are Utilized Since the sintered porous composite sheet according to the present Example has a high biobarrier property, the composite sheet is also particularly adaptable for use as an operative glove or cap. Such a glove or cap would be highly water resistant, air-permeable and elastic. Gloves employing the composite sheet have a remarkably improved fit and feel compared with that of conventional rubber gloves. The estimated biobarrier results of the glove or cap according to the Bacteria-permeability test method of FIG. 4 are enumerated in Table 3:

TABLE 3

| | Number of Raw Fungus | | | | | |
|---|---|---|---|---|---|---|
| Strain | P. diminuta | | | S. marcescens | | |
| Time (hr) | 0.5 | 1.0 | 6 | 0.5 | 1.0 | 6 |
| Example 4 (Sintered Composite Sheet) | <10$^2$ | <10$^2$ | <10$^2$ | 0 | 0 | <10$^2$ |
| B-Component Layer (Spunlace Nonwoven Fabric) | 10$^5$ | 10$^6$ | 10$^8$ | 10$^4$ | 10$^6$ | 10$^8$ |

EXAPLE 5

Sintering To Form A/B-Component Layer

Preparation of A-Component Layer and B-Component Layer

As another preferred example of the sheet, the A-component layer may comprise a bicomponent staple fiber (1.5 d×35 mm) having a PP core and a PE sheath. The A-component layer is preferably a carded web of about 20 g/m$^2$. The B-component layer has a specific weight of about 30 g/m$^2$. The B-component layer preferably comprises staple fibers comprising polyester (3 d×54 mm).

Formation of (A/B)-B-Component Layer

The web of A-component layer was laid on top of the web of B-component layer, and an A/B-component layer was entangled by a high pressure water stream. Thereafter, the combined web was hot air dried, leaving a multi-layered sheet of (A/B)-B construction.

Sintering Treatment

The above multi-layer web is then preferably sintered at a temperature of about 180° C. using an iron as in Example 3 above. A pliant sintered porous composite sheet is obtained.

Tape Landing Zone Utilizing Sintered-Film Surface

As mentioned previously, nonwoven fabrics may be used as, for example, the back sheet of diapers. These nonwoven back sheets require special tape landing zones. The multi-layered web of Example 5, when used as a diaper back sheet, dispenses with the need for special tape landing zones. A commercial adhesive tape for a diaper was tested for its re-release properties when adhered to the sintered porous composite sheet of Example 5. The composite sheet withstood the re-application test of the adhesive tape over ten times.

EXAMPLE 6

Sintering-Treatment with A/B-Component Layer Formation

Preparation of Mixed Web of A/B-Component

As another preferred example, about 60 parts of an easily melting bicomponent fiber (trade name "MELTY" made by UNITIKA, LTD.) was used as an A-component material and about 40 parts of viscose rayon (1.5d×45 mm, specific weight about 20 g/m$^2$) was used as a B-component material. The A and B component materials were mixed and carded resulting in a web having a specific weight of about 30 g/m$^2$. The bicomponent fiber had a polyester and a polyester derivative sheath. The A/B ratio was about 1.5

Preparation of (A/B)-B Multi-Layer Body

The A/B-mixed web is then laid on top of another rayon web of the B-component layer, subjected to a high-pressure water stream, and hot-air dried. A combined multi-layer body having an (A/B) -B layer is obtained.

Sintering Treatment

The above multi-layer body is then sintered at about 180° C. using an iron as in Example 3. A pliant film sheet is then obtained. When water was dropped on the surface of the A-component layer of this sheet, it was substantially instantaneously absorbed.

EXAMPLE 7

Application to Raw Material for Surgical Gown having Biobarrier Property

Preparation of Raw Material for A-Component Layer and B-Component Layer

A silicone resin was added to a combination of PP/PE to prepare a tow of fiber exhibiting water repellency (trademark "DF-72" made by DAIWABO CO., LTD.). The tow was then cut into 2d×5 mm segments while wetted with water containing a surface active agent. An A-component layer was formed thereby. The B-component layer comprises a spunlaced nonwoven fabric (about 30 g/m$^2$). The B-layer preferably comprises an antibacterial polynosic rayon (trademark "KITOPOLY" made by FUJIBO CO., LTD.) sized to about 1.5d×35 mm. The B-component layer is preferably water entangled.

Preparation of Layered Product of A-Component and B-Component Layers

The fiber is then made into a slurry, and passed through a wet pulp defibrillator to form extra fine fibers. The slurry is then applied around a cylinder paper machine to form a mat of extra fine fibers. The mat preferably has a basis weight of about 30 g/m$^2$. The mat is entangled using a series of nozzles having hydraulic pressures of about 40 kg/cm$^2$, 60 kg/cm$^2$, and 80 kg/cm$^2$. Then the mat is dried on a Yankee cylinder drum dryer. A layered sheet of A-component layer and B-component layer is obtained. The sheet has a surface gloss and is film-like, though fiber can be observed therein.

Sintering Treatment

The above sheet is then passed through a hot calendar-roller having a satin finished surface. The sheet is sintered at about 160° C. under a pressure of about 15 kg/cm$^2$. A soft sheet whose surface is transformed into an artificial leather-like state is obtained.

Estimation of Characteristics of Sintered Workpiece

A sheet manufactured according to the method above had the following properties:

- Air-Permeability: 15 sec/100 cc;
- Water-Resistance: 100 mm H$_2$O
- Contact Angle: 105 degrees
 (Water repellency was observed); and
- Bacteria-Permeability Test:
 P.diminuta only).

TABLE 4

|  | Number of Bacteria | | |
| --- | --- | --- | --- |
| Time (hours) | 0.5 | 1.0 | 6 |
| Sheet Before Sintering (Multi-Layer From Yankee) | Approx. 10$^3$ | Approx. 10$^3$ | Approx. 10$^4$ |
| Sintered Sheet | 0 | 0 | 0 |

The porous composite sheet was incorporated into surgical gowns. Compared with a conventional common nonwoven gown fabric (made by SONTALA, LTD.), the gowns with the porous composite sheet were said to exhibit improved breathability. Furthermore, blood applied under pressure against the surface of the gown did not stain.

EXAMPLE 8

Application to Diffusion Sheet or Absorbent Sheet

Preparation of A-Component Layer

As another preferred embodiment, a spunbond nonwoven fabric (trademark "ELVES" made by UNITIKA, LTD.; about 30 g/m$^2$) was drawn by about 1.2 times its unstretched length in the cross direction and by about 1.5 times its unstretched length in the machine direction while being heated to about 130° C. The nonwoven fabric comprises an easily fusible bicomponent fiber filament having a polyester core and polyethylene sheath. The final nonwoven fabric was drawn into a light weight fabric of about 16 g/m².

Formation of Composite of A-Component Layer and B-Component Layer

The A-component spunbond layer was fed along a stainless net. A B-component layer of about 100 g/m² basis weight comprises a soft wood pulp having a relatively long fiber. The B-component layer was placed on the A-component layer. After removing water from both layers, both layers were further subjected to a jet of high-pressure water of 70 kg/cm² to entangle the spunbond and the pulp layer. The sheet was then dried so that a multi-layer body sheet comprising an (A/B)-B-component layer was formed.

Sintering-Treatment of Multi-Layer Body (I)

The above multi-layer body is then passed through hot-calendar rollers having surface temperature of 180° C. under a pressure of 20 kg/cm². The resulting sintered sheet had a gloss coating. The resulting sheet is remarkably water-permeable, and quite useful for wiping. For example, when 5 cc of water is dropped on a flat glass and wiped with the sintered sheet, even fine water drops are thoroughly absorbed.

Application of Sheet to Sanitary Napkin

Figure 27:
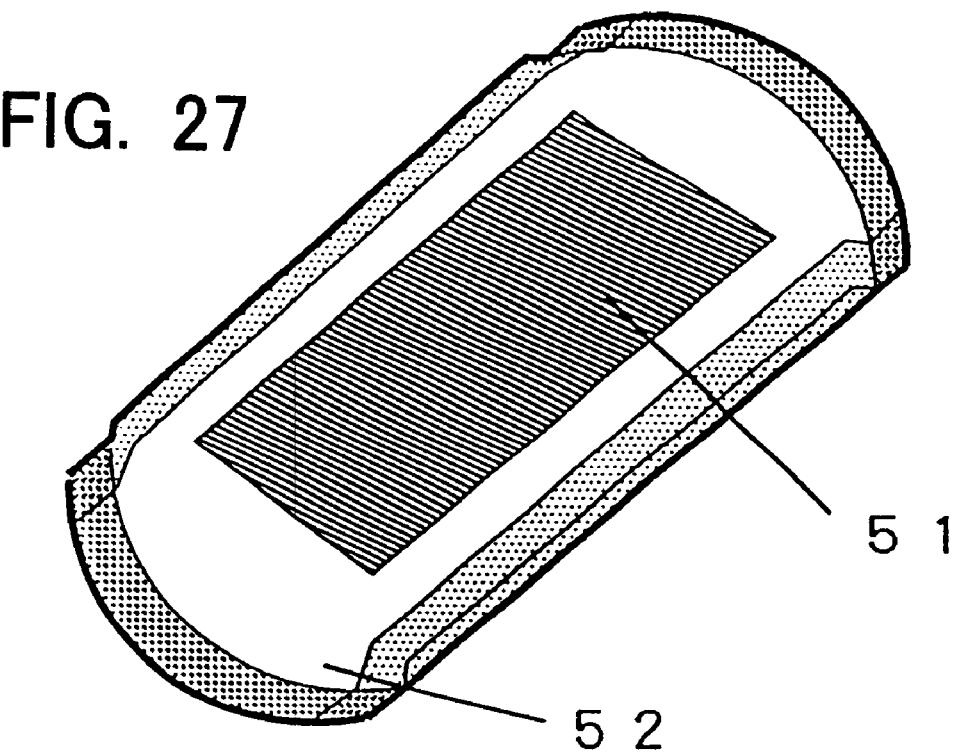
FIG. 27 is a perspective view of a product in which the sintered porous composite sheet of the present invention is used.
Figure 28:
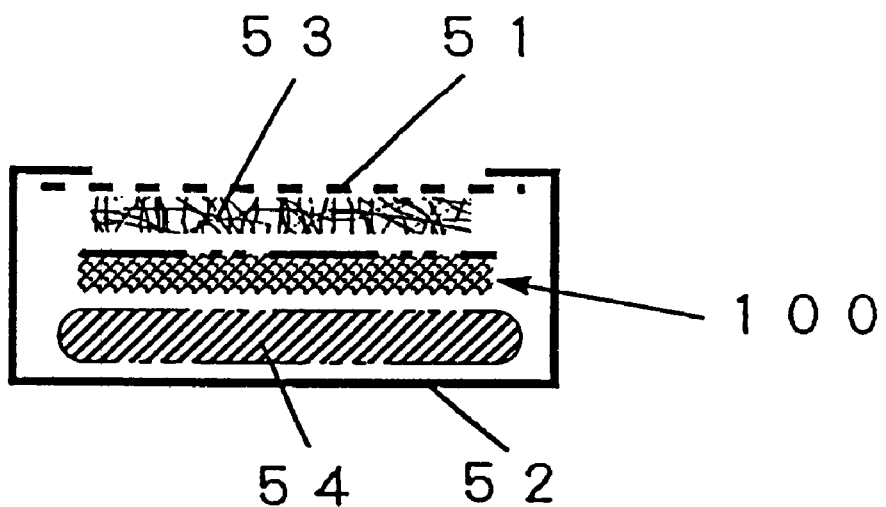
FIG. 28 is a longitudinal sectional view of FIG. 22.

The above sintered porous composite sheet may optionally be incorporated into a sanitary napkin. With reference to FIGS. 27 and 28, the napkin comprises a top sheet 51, a back sheet 52, a cushion web 53, and an absorbent material 54. The sintered porous composite sheet 100 is positioned between the cushion web 53 and the absorbent material 54. The absorbency speed and diffusion of the napkin were increased as compared with napkins without the sintered porous composite sheet.

Application of Sintered Sheet as Tip of Columnar Absorbing Bar

Figure 29:
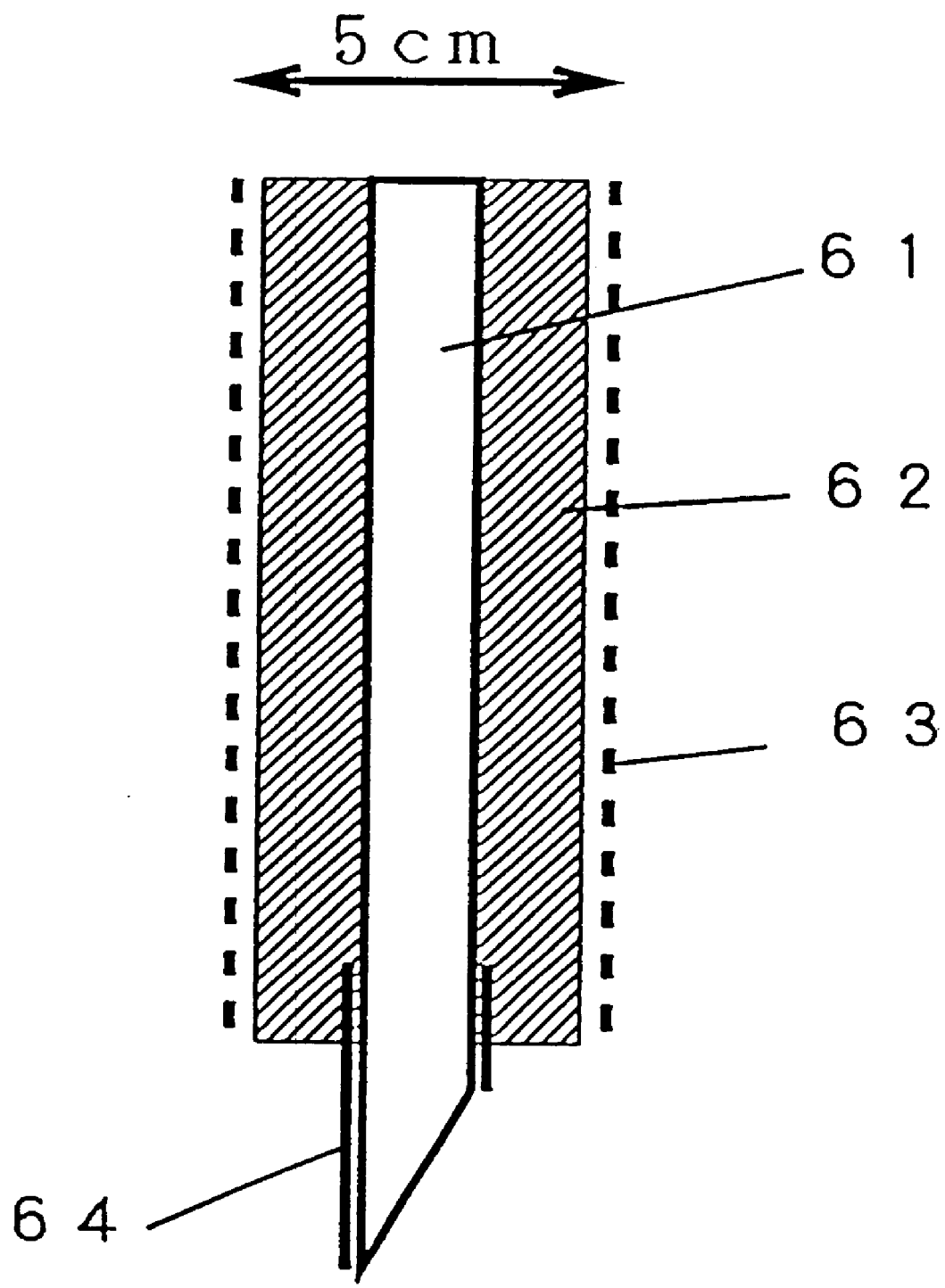
FIG. 29 is a longitudinal sectional view of a product in which the sintered porous composite sheet of the present invention is used.

A surgical body-fluid absorbing bar is shown in FIG. 29. The absorbing bar comprises a bar body 61 whose tip is obliquely cut. The bar is made of TCF (a cellulose spunbond made by NIMUTA CHEMICAL, LTD.); tissue paper 62; perforated polyethylene film 63; and a sintered porous composite sheet 64. The periphery of the bar body 61 is coated with the tissue paper 62. The paper 62 was coated with the polyethylene film 63. The tip projects from the coating and is wound with the sintered porous composite sheet 64. The surgical body-fluid absorbing bar has improved absorbing speed, holds the shape of the tip and does not attract lint.

Preparation of Multi-Layer Body (II) Obtained by CMC-Treatment of Multi-Layer Body (I)

The above multi-layer body (I) was immersed in a mixed liquid which comprises about 10% sodium hydroxide, about 35% potassium monochloroacetate, about 1% epichlorohydrin, and about 54% water for a period of about one minute. Thereafter, the multi-layer body (I) was maintained at a temperature of about 60° C. for a period of about four hours so as to be partially transformed into a CMC. Then, the multi-layer body (I) was immersed in an aqueous methanol solution of about 70%, and was dried with methanol of about 100%. The degree of substitution of carboxymethyl group was about 0.47. The pure-water absorbing amount of this CMC-treated multi-layer body (II) was about 27 g/g.

Sintering-Treatment of Multi-Layer Body (II)

The above CMC-treated multi-layer body (II) was passed between hot-calendar rollers having a surface temperature of about 180° C., under a pressure of about 15 kg/cm², and sintered. The surface was transformed into a film, and had a coat-paper-like morphology.

EXAMPLE 9

Partially Sintered Formation in Which Top Sheet, Absorber and Back Sheet are United

Preparation of Stretching Back Sheet

A cellulose nonwoven fabric and an elastic film were combined with each other to form a composite stretching back sheet. The cellulose nonwoven fabric is preferably a spunlaced nonwoven fabric prepared by introducing a parallel card web (specific weight of 40 g/m²) which was obtained from a viscose rayon staple (1.5d×35 mm), into a high-pressure stream entangling apparatus. This nonwoven fabric may be elongated by about 200% in the cross direction (CD).

An elastic film comprising T.P.U. and having a specific weight of about 40 g/m² was prepared. The film and the nonwoven fabric were laminated over substantially all of the surfaces thereof with hot-melt so as to obtain a back sheet which may be stretched to about 150%. The laminated cellulose nonwoven fabric functions as a B-component layer in the present working example.

Preparation of A-Component Layer

A spunbond (trademark "ELVES" made by UNITIKA, LTD.; 26 g/m²) bicomponent filament fiber comprising polyester as a core and polyethylene as a sheath was prepared.

Partially Sintering A-Component Layer and B-Component Layer

A wave was formed in the spunbond (the A-component layer) along channel 11a as shown in FIG. 15, while the upper side of the nonwoven fabric was filled with SAP (trademark "IM-3000" made by SANYO CHEMICAL INDUSTRIES, LTD.) and a granulated composite comprising peat moss and acetate. The cellulose section (the B-component layer) of the back sheet was laminated thereto. Contact areas were heated at a temperature of about 180° C. under a pressure of about 15 kg/cm² at the side of the urethane film having heat resistance, so that the A-component layer was melted and bonded under pressure to form band-like sintered areas. Thereafter, the whole was compressed while cooled and deformed into a thin sheet shape as shown in FIG. 16(a). The SAP/acetate/peat moss composite was conjugated to the surface of the B-component layer to form the composite shown in FIG. 18(a).

According to this process, a composite is obtained in which the A-component layer functions as a top sheet, and the B-component layer functions as a diffusion sheet, an absorbent and a back sheet. When such a composite is applied to a diaper, excreted urine is speedily absorbed into the B-component layer through the sintered areas and diffused for absorption by the polymer component. During use, the wave changes from that as shown in FIG. 16(a) to an erect position due to a swelling as shown in FIG. 16(b). Since the wave portions are hydrophobic, there is no liquid leakage from the crests thereof. The skin of a baby typically contacts this portion so the skin is isolated from urine and feces.

EXAMPLE 10

Preparation of A-Component Layer and B-Component Layer

A card web was prepared as an A-component layer. The carded web comprises a high contractile PE/PP bicomponent fiber (PNE fiber made by DAIWABO CO., LTD.) having 2×45 mm. The B-component layer comprises a viscose rayon 30 g/m$^2$ having 1.5d×45 mm.

Figure 30:
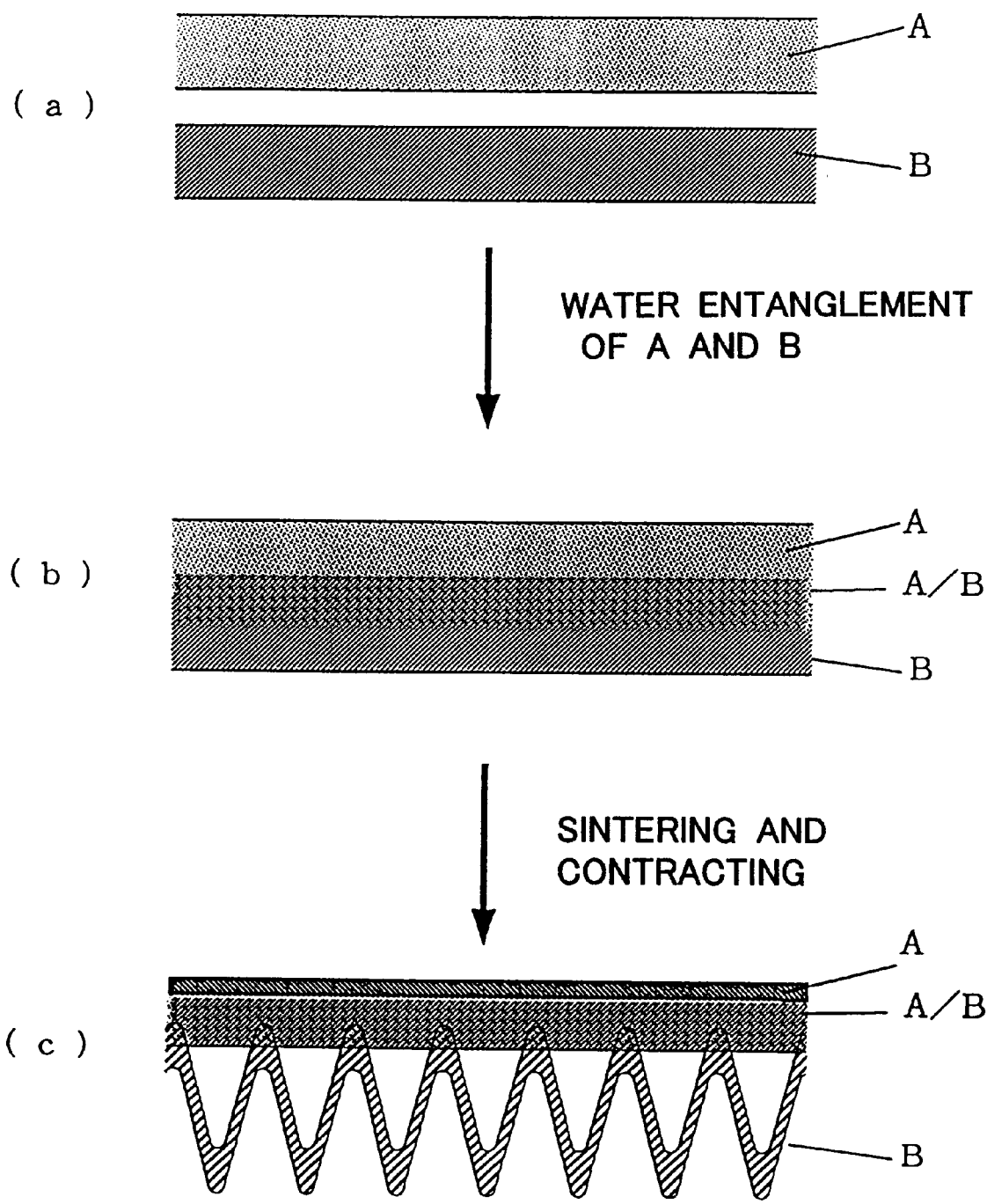
FIG. 30 is a schematic diagram which illustrates the embodiment of FIG. 16.

Formation of Three-Layered Structure by Water-Stream Entangling A-Component Layer and B-Component Layer The above A-component layer and B-component layer were laid on top of each other and passed through a nozzle line comprising three high-pressure nozzles (about 30 kg/cm$^2$, 70 kg/cm$^2$, 75 kg/cm$^2$). The composite was then subjected to hot air drying at a temperature of about 80° C., forming a multi-layer nonwoven fabric having about 45 g/m$^2$ (FIG. 30(a)). This nonwoven fabric had a structure which is typically illustrated as shown in FIG. 30(c).

Heat Contraction and Sintering Treatment

The above multi-layer nonwoven fabric was heated at about 130° C. without being stretched. A three-dimensional nonwoven fabric having a specific weight of about 100 g/m$^2$ was obtained. The A-component layer remained relatively flat while the B-component layer had a plurality of loops.

Next, the composite was passed between a flat roller heated to about 180° C. to which a Teflon (trade name) coating had been applied and a silicone rubber roller, under a pressure of 4 kg/cm$^2$. The flat surface of the three-dimensional nonwoven fabric contacted the flat roller, while the side with the loops contacted the silicone rubber roller. Accordingly, the A-component and B-component were sintered, resulting in a sintered porous composite sheet having a structure as shown in FIG. 30(b).

Utilization for Female Member of Velcro Zipper

The B-component layer having a three-dimensional loop structure was combined with a film having hooks (made by 3M CO., LTD.). The B-component layer was used as a female member of a Velcro zipper, while the film was used as a male member thereof. This zipper had a remarkably high degree of coupling.

When the composite sheet is used as the means of securement in a disposable diaper (female member), the female member is adhered to the diaper back sheet.

Application to Storage Carrier of Powdered Polymer Having High Absorbing Property A multi-layer sheet having the folded surface as described above has both voids due to a large fold structure thereof as well as absorbing characteristics along the sintered surface. When these two characteristics are utilized, a powdered polymer having a high absorbing property can be relatively stably stored in a large amount to about 20 g/100 cm$^2$ in the fold loop. A very compact absorbent which is excellent in absorbing property and diffusing property is realized.

Figure 31:
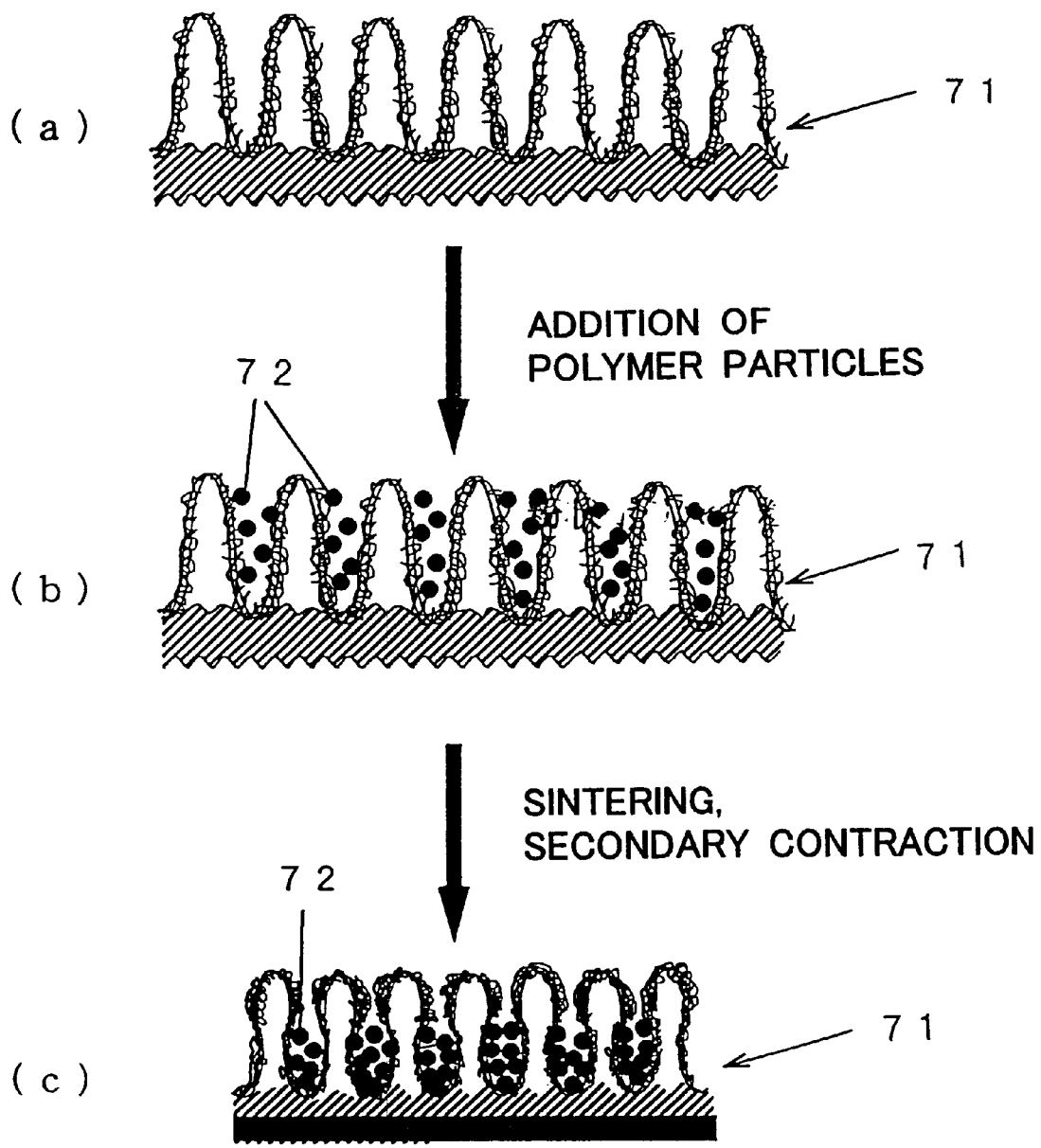
FIG. 31 is a schematic diagram which illustrates the embodiment of FIG. 17.

Namely, as shown in FIG. 31(b), a highly absorbent powdered polymer 72 is introduced into the hollows of the multi-layer sheet 71. As shown in FIG. 31 (a), the multi-layer sheet 71 has a loop-shaped surface formed during the above-described first contraction treatment. Since the powdered polymer 72 may easily escape the hollows, a further contraction is necessary while the surface is subjected to a sintering treatment. The space between the adjacent crests is narrowed, and the polymer particle 72 is locked in the storage sites. If necessary, the powdered polymer 72 may be more stably locked in place by absorbing a small amount of moisture. Alternatively, the surface of the fold sheet may be coated with a tissue, a film or the like, to further lock the powdered polymer 72 in place.

EXAMPLE 11

Sintered Porous Composite Sheet Combined with Cellulose Absorbing Sheet

Preparation of A-Component Layer and B-Component Layer

The A-component layer comprises a spunbond nonwoven fabric (trade name "ELVES" made by UNITIKA, LTD.; 25 g/m$^2$) having a bicomponent fiber filament was prepared as an A-component layer. The fiber filament comprises polyester as a core and polyethylene as sheath. The B-component layer comprises a sheet of trade name "TEXEL" (a specific, weight of 100 g/m$^2$) made by Shin-Oji Paper Co. Ltd. The B-component sheet is formed by stream-entangling a wood-pulp and a PP spunbond.

Conjugation and Sintering Treatment of A-Component Layer and B-Component Layer

The A-component layer was laid on top of the B-component layer resulting in about a 4.5 mm thick composite. A silicone released paper was placed on the A-component layer, and heated with an iron to about 180° C. for a period of about one minute. Accordingly, the A-component and B-component were sintered, forming a pliant coat-paper-like sheet having a surface gloss. This sheet had a thickness of about 2.1 mm.

Water Holding Property and Low-Dust Property of Sintered Porous Composite Sheet

The sintered porous composite sheet was readily liquid absorbent. Furthermore, little dust from the absorbing layer was observed. Test results for this embodiment are as follows:

| | |
|---|---|
| Water-Absorbing Speed | 2 sec/100 cc |
| Rewetting | 0.01 g or less |
| Dust from Workpiece | 0.01 g or less |

Application of Chemical to Sintered Porous Composite Sheet

Aqueous polyethylene glycol solution and an aqueous organic carboxylic acid solution were absorbed in the B-component layer in an amount of 10 g/m$^2$. The sheet so impregnated is particularly adaptable for use as a dust wipe.

Application to Wipes for Room Cleaning

The dust absorbency of the composite was tested. After many repeated uses, dust and other coarse particulates were stably absorbed in the composite. Furthermore, moisture was also removed.

EXAMPLE 12

Top Sheet in Which Bicomponent Fiber Incorporated

Preparation of Hydrophobic A-Component Layer P

The A-component layer comprises a spunbond nonwoven fiber (trade name "ELVES" made by UNITIKA, LTD.) having a bicomponent fiber of PET as a core and PE as a sheath. This nonwoven fiber was about 2 deniers, specific weight of about 20 g/m$^2$, apparent specific gravity of about 0.09 g/m$^3$ and water repellency. No water permeability was observed under normal pressure.

Preparation of Hydrophilic B-Component Layer

The B-component layer comprises a card web of 25 g/m$^2$ having a bicomponent fiber staple (trade name "SOFIT" made by KURARAY CO., LTD.) of 3d×51 mm of PET as a core and PE as a sheath. The B-component layer was made to be hydrophilic. This nonwoven fabric had an apparent specific gravity of about 0.06 g/m$^3$.

Sintering Treatment of A-Component Layer and B-Component Layer

The above A-component layer and B-component layer were laid on top of each other according to a pattern as shown in FIG. 26. Only the area to be formed into an A/B-component layer was heated and pressed at about 130° C. and about 10 kg/cm$^2$ from the side of the B-component layer. The heated and pressed area was almost completely melted and conjugated to such a degree that surface destruction was caused.

Application to Diaper

Figure 32:
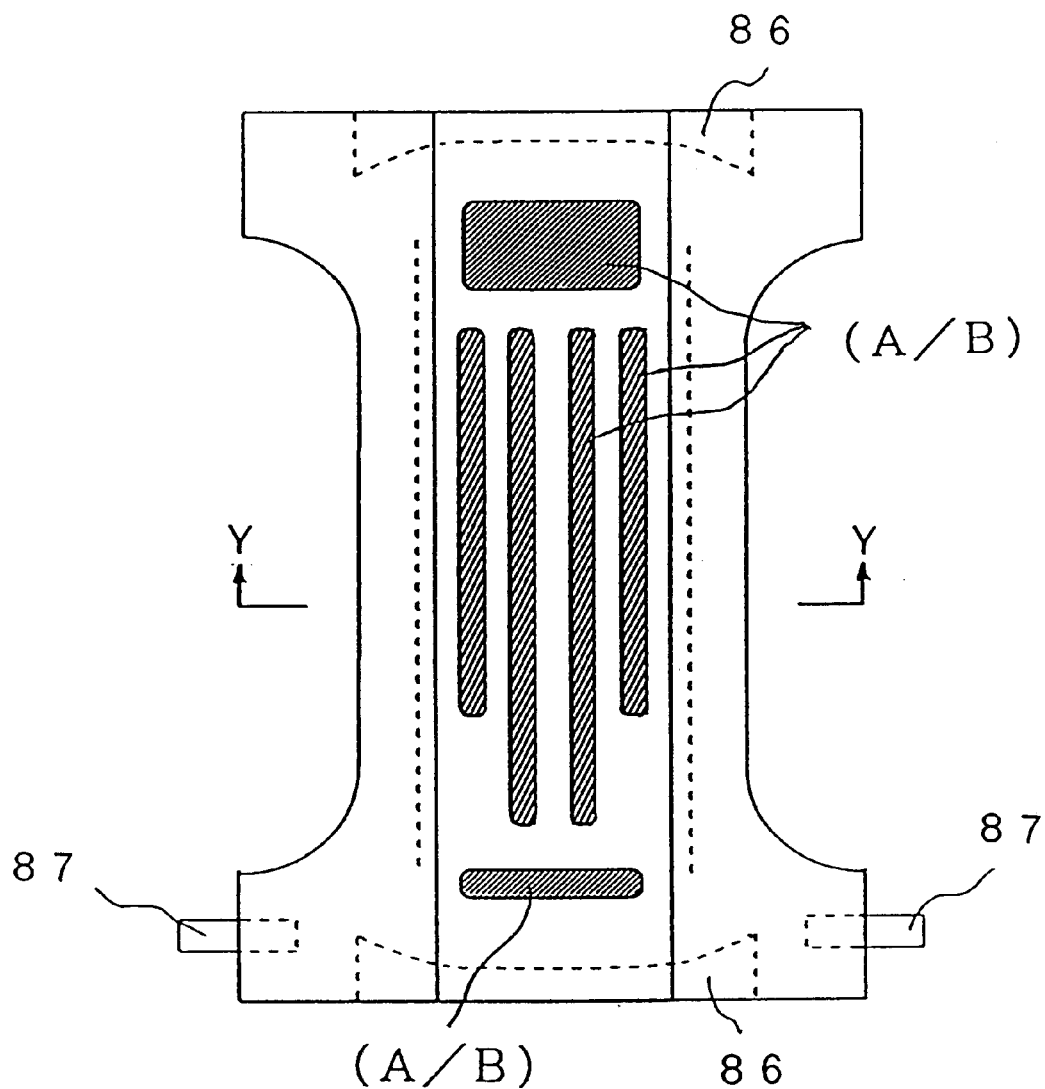
FIG. 32 is a plan view of a disposable diaper in which the water-permeable composite sheet of the present invention is used.
Figure 33:
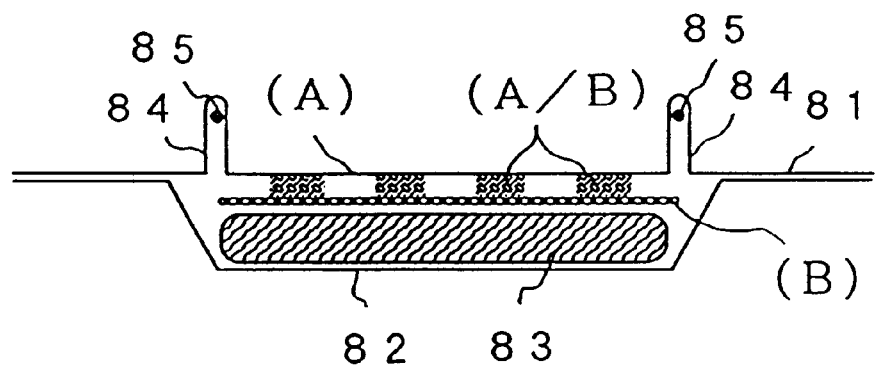
FIG. 33 is a schematic longitudinal section taken along line Y—Y in FIG. 32.

Each of FIGS. 32 and 33 illustrates a diaper to which the water-permeable composite sheet obtained by the above treatment is applied. The diaper comprises a back sheet 82; a top sheet 81; an absorbent 83; a standing gather 84 containing an elastic 85; a waist gather 86; and a closure means 87. The top sheet 81 is preferably a unitary hydrophobia material extending from side to side. The A/B component layer in the top sheet 81 can be, for example, the above-mentioned structure as shown in FIGS. 23 or 24.

An absorption test of 80 cc × three times was carried out. Rapid water permeation and absorption were observed in the sintered A/B-component layer. Even after absorbing water three times, the A-component layer and the B-component layer were not separated. Rewetting occurred about 0.2 cc or less for the first time, and about 1 cc or less for the second time, and about 1 cc or less for the third time.

EXAMPLE 13

Application to Food Packaging Material

A hydrophobic A-component layer and a hydrophilic B-component layer which are substantially the same as the layers used in Example 1 were laid on top of each other. The layers were heated and pressed by a pair of chromium-plated rollers having flat surfaces, which had been heated to about 140° C. under a pressure of a gage pressure of 3 kg/cm$^2$. A paper-like sheet whose surface was deformed into a film was obtained. The A-component layer and the B-component layer of this sheet were nearly completely fused.

A PE-film having a thickness of about 20/μm was laminated to the B-component layer to form a three-layer body. The resulting body was folded as a pouch having a gusset, which had a volume of about 200 cc and was opened at one side only. A frozen bun was put into this pouch and sealed. The pouch was heated in an oven for a period of thirty minutes. The pouch was then allowed to cool for twenty minutes, and then opened. Water drops were not observed on the surface of the bun nor did the pouch cling to the bun.

EXAMPLE 14

Application to Sanitary Materials

A hydrophobia PP-spunbond nonwoven fabric (18 g/m$^2$) was used as an A-component layer. The B-component layer comprises a homogeneously mixed carded web of about 30 g/m$^2$ comprising about 50% of a bicomponent fiber (trade name "ES Fiber" made by Chisso Co., Ltd.) of 2d×51 mm and about 50% of a polyester fabric (trade name "BACTE-KILLER" made by KANEBO, LTD.) of 3d×51 mm was prepared. The bicomponent fiber comprised PE/PP and had a sheath and core. The polyester was made hydrophilic by treating it with a surface active agent containing silver and zeolite.

Sintering of A-Component Layer and B-Component Layer

The above B-component layer was laid on top of the above A-component layer and passed through a pair of rollers. One of the pair was a paper roller and the other a chromium plated roller. The layers were pressed at a rate of about 10 m/min at about 2 kg/cm$^2$. The A-component layer contacted the chromium plated roller which had been heated to about 120° C. Accordingly, both layers were sintered together. As a result, the A-component layer was transformed into a film, while the B-component layer had a rough nap so that water was readily absorbed.

Utilization as Surface Material of Diaper

The composite was incorporated as a top sheet of an adult diaper with the A-component layer contacting the body. The diaper was tested by applying 100 cc of liquid at 30 minute intervals with the following results:

| First Application  | 100 cc: 25 sec |
|--------------------|----------------|
| Second Application | 100 cc: 33 sec |
| Third Application  | 100 cc: 40 sec |

The rewet value after the third absorption was 1.2 g/100 cm$^2$, demonstrating a remarkably absorbent product.

Utilization as Cushion Material for Diaper

The composite sheet was inserted between a PP spunbond top sheet and the absorbent so that the B-component layer contacted the top sheet, and the A-component layer contacted the absorbent. An absorption test was carried out. The "Blank" was a prior art disposable diaper.

TABLE 5

|  | Absorbing Speed (sec) | |
| --- | --- | --- |
|  | Sample | Blank |
| First Application (50 cc) | 18 | 28 |
| Second Application (50 cc) | 25 | 38 |
| Third Application (50 cc) | 32 | 45 |
| Rewetting (g/100 cm$^2$) | 1.6 | 2.6 |

According to the above results, the incorporation of a sheet in the present working example remarkably increases absorbing speed. Rewetting is also reduced.

EXAMPLE 15

Application to Blanket Cover and Sheets Used in Hospital

Preparation of Hydrophobic A-Component Layer

The A-component layer comprises a card web having a specific weight of about 15 g/m$^2$. The A-component layer was prepared from a blended fiber comprising (1) about 50% of a hydrophobic PP/PE-bicomponent fiber staple (trade name "ES FIBER" made by Chisso Co., Ltd.) of 2d×45 mm in which a spinning oil solution was added, and (2) about 50% of a PET fiber of 1.5d×45 mm.

Preparation of Hydrophilic B-Component Layer

The B-component layer comprises a card web having a specific weight of about 20 g/m$^2$ and is prepared from a blended fiber comprising about 30% PP/PE-bicomponent fiber staple (similar to the one used as the A-component layer) and about 70% of a rayon fiber (trade name KITO-POLY made by Fujibosekl Co., Ltd.) of 1.2d×35 mm. The A-component layer and the B-component layer are laid on top of each other, and passed through a hot air conveyer at about 130° C., so that the A-component layer and the B-component layer are thermally joined with each other.

Sintering of A-Component and B-Component Layers

The above thermally joined sheet was passed through rollers so that the A-component layer contacts a heating roller of 50 cm diameter. The heating roller was heated to about 140° C., and the composite was fed therethrough at about 2 sec/meter. The surface of the A-component layer was transformed into a film. This sheet exhibited excellent water absorbency, and was suitable for antibacterial applications.

EXAMPLE 16

Application Meat Package and Tray

Preparation of Hydrophobic A-Component Layer

The A-component layer comprises a spunbond nonwoven fabric of about 20 g/m$^2$ (trade name "ELVES" made by UNITIKA LTD.) having a bicomponent fiber of PET core and PE sheath. The B-component layer comprises a mixed card web comprising about 60% of a PE/PET-bicomponent fiber of 2d×45 mm which was rendered hydrophilic, and about 40% of a high absorbing fiber (trade name "VEROASIS" made by KANEBO, Ltd.) of 3d×51 mm treated in a hot air conveyer, and having a basis weight of about 30 g/m$^2$.

Sintering A-Component Layer and B-Component Layer

The A-component layer and B-component layer are then superposed and passed between a chromium-plated roll heated to about 150° C. and a paper roll at a pressure of about 2 kg/cm$^2$, with the A-component layer facing the chromium-plated surface. A water permeable composite sheet is obtained. The surface of the A-component layer became film-like and the B-component layer retained its non-woven fabric nature.

The water permeable composite sheet had excellent water permeability from the top surface to the back surface of the A-component layer, and exhibited one-way water permeability, keeping the surface of the A-component layer dry.

The above water permeable composite sheet was laid on a polystrol food tray with the A-component layer facing up, A cut of frozen beef was placed thereon, and wrapped. The steak was then thawed, upon which no drippings were observed.

EXAMPLE 17

Application to Super Thin Sanitary Napkins

Preparation of Hydrophobic A-Component Layer

The A-component layer comprises a three-layer non-woven fabric (trade name "UNICELL" manufactured by TEIJIN, Co.) of PP fibril burst fibers surrounding a core layer of PET filament web. The three layers were integrated by heat and pressure.

Preparation of Hydrophilic B-Component Layer

The B-component layer comprises a highly water absorbent material (trade name "CM modified TECCEL" manufactured by SHINOJI, Co.) which consists of a non-woven fabric formed by water entangling a PP spun bond (12 g/m$^2$) with wood pulp (80 g/m$^2$), and subjected to carboxymethylation treatment.

Sintering A-Component Layer and B-Component Layer

The A-component layer and the B-component layer were superposed, and heated under pressure at about 140° C. from both sides. The surface of the A-component layer was transformed into film. The water permeable composite sheet had a rapid liquid take-up speed and excellent absorbency.

A PE film was positioned above the water permeable composite sheet on the B-component side. A test sample of artificial blood was applied to the composite. The composite showed rapid absorbing speed and less than 0.1 cc of rewet.

Figure 34:
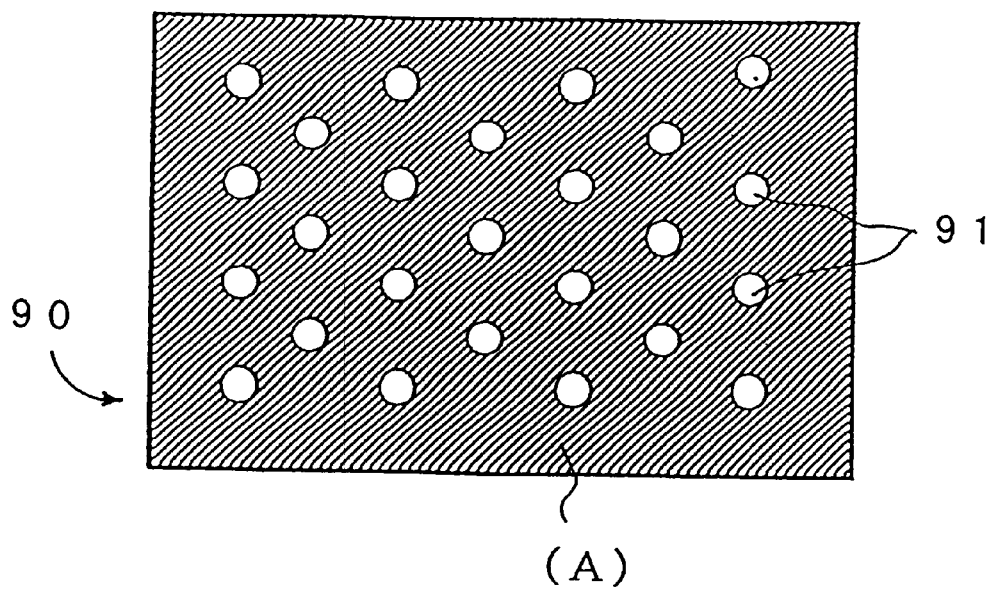
FIG. 34 is a longitudinal sectional view of the water-permeable composite sheet of another preferred embodiment of the present invention.
Figure 35:
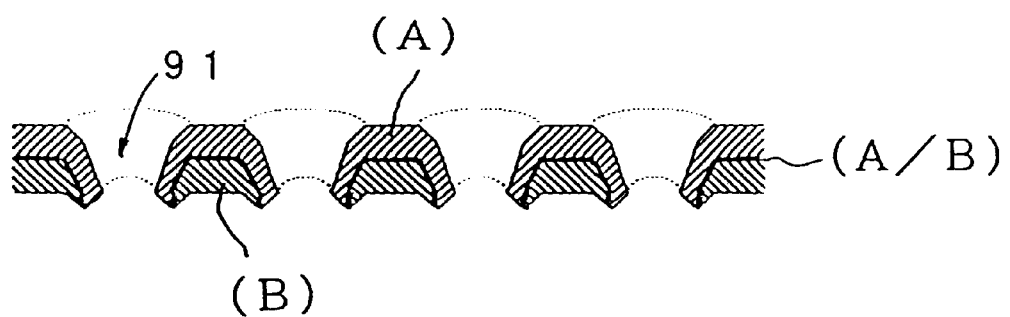
FIG. 35 is a longitudinal sectional view of the water-permeable composite sheet of FIG. 6.

The balance between maintaining a stain free property and porosity is important. With reference to FIG. 34, a water permeable composite sheet 90 comprising an A/B component layer is formed by sintering the entire surface of the A-component layer and B-component layer. Pores 91 are formed thereby. The pores 91 preferably have a diameter less than 1 mm and provide improved liquid retention. Pores 91 advantageously avoid close contact with the skin, as well as separate the solid component from the liquid component in its place. Pores 91 alternatively do not penetrate through the sheet, and may rather be a deep emboss.

EXAMPLE 18

Preparation of Hydrophobic A-Component Layer

The A-component layer comprises a PE/PET bicomponent spunbond nonwoven fabric (trade name "ELBES"

manufactured by YUNICHIKA, Co.). The hydrophilic B-component layer is formed from a polyester continuous pore urethane foam sheet (foam rate : 40 times, specific gravity: 25 kg/cm$^3$) sprayed with super absorbent polymer (SAP), and a web (basis weight about 30 g/m$^2$) consisting of about 60% of hydrophilicated 2d×45mm PE/PET fibers (trade name "SOFIT" manufactured by KURARE, Co.) and about 40% of 1.5d×45 mm viscose rayon fibers. The two B-component layers were punched to form an absorbent sheet wherein the pores of the urethane foam and the spaces between fibers were filled with SAP.

Sintering A-Component Layer and B-Component Layer

The A-component layer and B-component layer were superposed and passed between a stainless roll (heated to have a surface temperature of 120° C.) and flat surface chromium-plated roll (not heated) at a pressure 6 kg/cm$^2$ gauge, with the A-component layer facing to the stainless roll for sintering. Prior to sintering, the A- and B-component layers were about 8 mm thick. After sintering, the layers were compressed to about 2.2 mm. In the absorbent sheet thus obtained, the A-component layer and B-component layer were closely joined together by fusion of the PE component in each, and exhibited rapid liquid take-up on the A-component layer side.

Water Absorption Test

The sheet was laid so that the A-component layer was facing up. Upon application of water, the sheet increased to about 15 mm or 7 times its dry thickness. The sheet retained its strength and integrity. As with SAP containing absorbent products, the saturated article had the feel of hard jelly.

Figure 36:
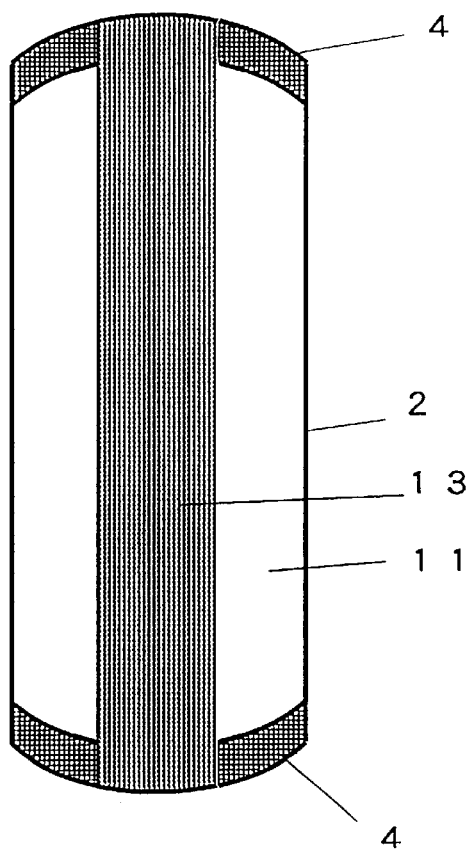
FIG. 36 is a plan view which illustrates an absorbent product according to another preferred embodiment.
Figure 37:
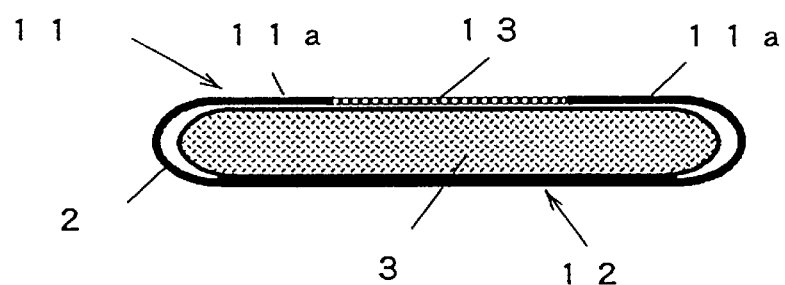
FIG. 37 is an enlarged sectional view of the absorbent product shown in FIG. 36.

In FIGS. 36 and 37, the absorbent article is formed as a sanitary napkin. There, a tubular sheet material 2 has a substantially rectangular absorbent body 13. Both ends of the sheet material 2 are sealed at 4. Sheet material 2 comprises an inner sheet portion 11 for contacting the skin when worn, an outer sheet portion 12, and a liquid permeable area 13 having about one third of the total width of the article. The inner sheet portion 11 is liquid substantially impermeable only at area 13. The areas 11a disposed at opposing sides of area 13a have low liquid permeability. The outer sheet portion 12 consists of liquid impermeable material.

Figure 38:
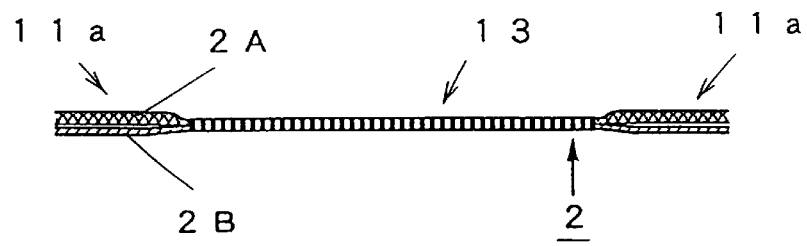
FIG. 38 is an enlarged sectional view of elements of the inner sheet shown in FIG. 36.

The inner sheet portion 11, as illustrated in section in FIG. 38, comprises an A-component layer 2A of hydrophobic material superposed on a B-component layer 2B of hydrophilic material. The A-component layer and B-component layer are mutually integrated by sintering at the liquid permeable area 13. In the lower liquid permeable area 11a, the A-component layer and B-component layer exist independently, even if they contact one another. On the other hand, in the liquid permeable area 13, the A-component layer and B-component layer are mutually integrated so that the easily fusible A-component layer is diffused inside of the thermally stable hydrophilic B-component layer. Therefore, the liquid permeable area 13, while having low hydrophilic tendencies, is nevertheless highly liquid permeable.

When liquid contacts such an absorbent article, the liquid permeates the central liquid permeable area 13 and is absorbed by the absorbent body 3. In addition, since the surface has a low hydrophilic property at its surface, a dry feeling is maintained. Furthermore, the low liquid permeable areas 11a are provided at both sides of the liquid permeable are 13, so side leakage and wet-back are substantially eliminated.

Figure 39:
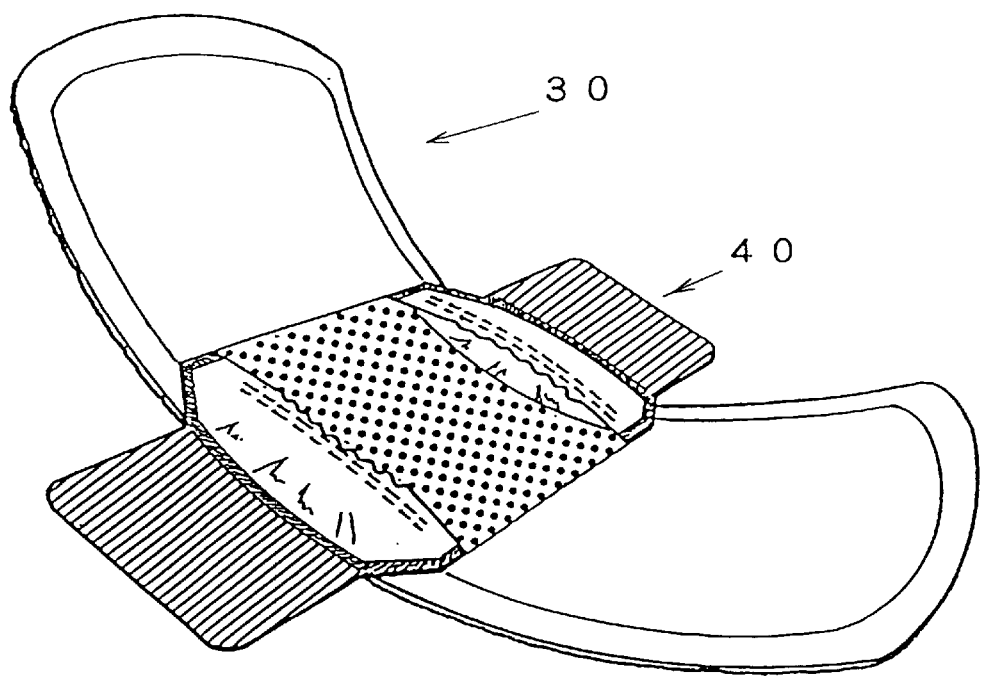
FIG. 39 is a perspective drawing of an absorbent product according to another preferred embodiment.
Figure 40:
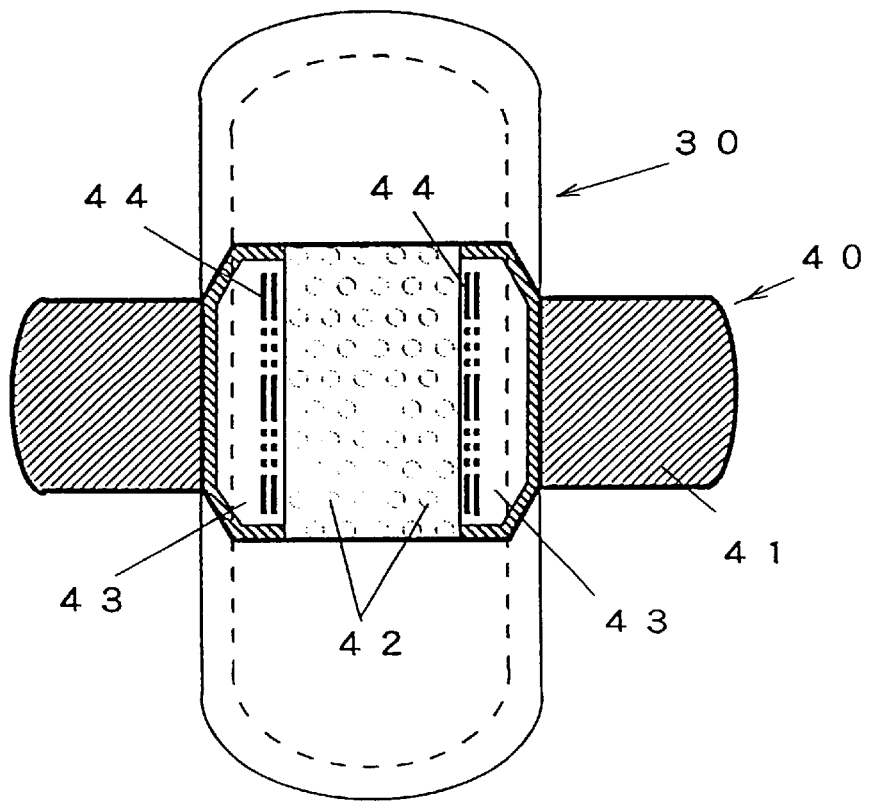
FIG. 40 is a plan view of the absorbent product in FIG. 39.

FIGS. 39 and 40 show another preferred embodiment in which the invention is applied to an absorbent body. The absorbent body comprises a liquid permeable top sheet material, a liquid impermeable back sheet material, an absorbent body 30 having a conventional structure disposed therebetween, and a liquid controlling unit 40 disposed at approximately a central portion along the lengthwise direction of the absorbent body 30. The controlling unit 40 has a substantially rectangular configuration and is attached to the absorbent body 30 by any suitable means such as a heat seal. Optionally, wings 41 may be provided to extend beyond the side edges of the absorbent body.

Figure 41:
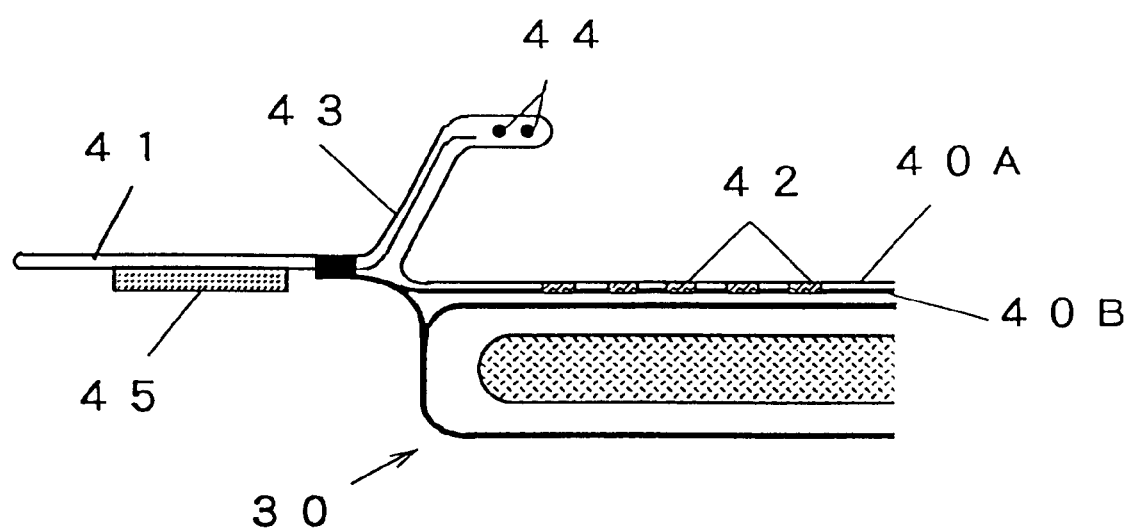
FIG. 41 is a sectional view of the absorbent product shown in FIG. 7.

As seen from the cross section shown in FIG. 41, the controlling unit 40 comprises, like the embodiment shown in FIGS. 39 and 40, an A-component layer of easily fusible material superposed on a B-component layer having a higher heat resistance than the A-component layer. The A- and B-component layers are mutually integrated by sintering at a plurality of substantially round portions 42 to form a liquid permeable area. The sintered liquid permeable portion has a low hydrophilic property, but a large liquid permeability as mentioned above.

Part of the A-component layer forms cuffs 43 extending from both sides thereof. An elastic member 44, such as a rubber strip, is encased by cuffs 43. When worn, cuffs 43 stand under the influence of the elastics 44 to form a barrier as shown in FIG. 41. A pressure sensitive adhesive layer 45 is provided on one surface of the wings 41.

Liquid applied on the controlling unit 40 penetrates through the sintered liquid permeable area 42 and then is absorbed by the inner absorbent body 30. Even when a larger amount of liquid is applied, side leakage is prevented by cuffs 43. Wings 41 and cuffs 43 are preferably formed by an extension of the A-component layer 40A.

As has been stated, the porous composite sheet of the present invention comprises at least two porous materials, one of which is an easily fusible material and permeates the spaces of the porous material having higher thermal stability. By carefully selecting the materials and manufacturing conditions of the sintering, it is possible to obtain a porous composite sheet having varying degrees of porosity over a wide range of desired absorbency. The combination of a first hydrophobic material and a second hydrophilic and porous material is optimum for various sanitary and medial articles. The composite sheet is generally permeable to air or moisture.

Furthermore, in the sintered porous composite sheet of the present invention, excellent biobarrier properties are realized using a water repellent micro-fibril layer as a first porous layer and a hydrophilic cellulose layer as a second porous layer. In this case, the composite sheet is readily suitable for surgical applications such as surgical gowns, drapes, masks and the like. Also, such a composite sheet is suitable for filters for vacuum cleaners due to its multi-layer microporous structure and dust preventing properties. In addition, according to the method of the present invention, the above sintered porous composite sheet is easily manufactured on an industrial scale.

While the invention has been described in connection with the preferred embodiments, the invention is not restricted thereto. It will be readily appreciated by those skilled in the art that these embodiments are subject to modifications which are within the scope of the invention as defined by the appended claims.

What is claimed is:

1. A method for controlling the permeability characteristics of a sintered composite sheet comprising the steps of:

providing a first layer comprising an A-component having a first melting temperature;

providing a second layer comprising a B-component having voids and a second melting temperature higher than the first melting temperature;

superimposing said first layer on said second layer to form an interface surface between said first layer and said second layer;

selecting a sintering site distribution, a sintering temperature, and a sintering pressure based on desired permeability characteristics, said sintering temperature being greater than or equal to the first melting temperature and less than the second melting temperature;

sintering said first layer and said second layer in said selected sintering site distribution at said selected sintering pressure and sintering temperature to thereby form sintered sites of an A/B-component at said interface surface, the A/B-component being formed by the A-component melting and flowing into the voids of the B-component while the B-component is substantially dimensionally stable; and allowing said sintered sites to cool to form said composite sheet and thereby control the permeability thereof.

2. The method of claim 1, further comprising the steps of:

entangling said first layer and said second layer to form a three-layer composite comprising an A-component layer, an A/B-component layer, and a B-component layer.

3. The method of claim 2 wherein said step of entangling comprises applying a high pressure stream of water to said superimposed first and second layers.

4. The method of claim 2 wherein said step of entangling comprises using a needle punch to entangle said first layer and said second layer.

5. The method of claim 1, wherein said A-component comprises a spunbond non-woven fabric and said B-component comprises a pulp fiber mat, said method further comprising the step of:

subjecting said first layer to a jet of high-pressure water to cause said spunbond non-woven fabric of the first layer to be entangled within said pulp-fibers of said second layer.

6. The method of claim 1, wherein said A-component comprises a carded polyolefin synthetic fiber web and said B-component comprises cellulose fibers, said method further comprising the step of:

applying a high-pressure stream of water to said first layer and said second layer while superimposed.

7. The method of claim 1 wherein said sintering site distribution substantially covers the entire interface surface of the composite sheet to thereby control the permeability of said composite sheet.

8. The method of claim 1 wherein said sintering site distribution is a patterned array over at least a portion of the interface surface of said composite sheet designed to control the permeability of said composite sheet.

9. The method of claim 1 wherein said second layer is hydrophilic.

10. The method of claim 1 wherein the first melting temperature is at least about 30° C. lower than the second melting temperature.

11. The method of claim 1 wherein said A-component is selected from the group consisting of polyethylene, polypropylene, polyethylene terephthalate, styrene ethylene butadiene styrene block copolymer, styrene isoprene styrene block copolymer and styrene ethylene propylene styrene block copolymer.

12. The method of claim 1 wherein said A-component is selected from the group consisting of cellulosic material, polyurethane, polyvinyl alcohol, polyphenol polyacrylonitrile, polyester, and nylon.

13. The method of claim 1 wherein said A-component is selected from the group consisting of melt-blown non-woven fabric, wet-formed synthetic pulp, foam extruded net, molten extruded high-fibrillated net, spunbond non-woven fabric, and carded non-woven fabric.

14. The method of claim 1 wherein said B-component is selected from the group consisting of a foam sheet, air-laid wood-pulp sheet, a fiber mat, tissue paper, rayon-web, cotton-web, cellulose web, polyacrylonitrile-fiber web and synthetic-fiber web.

15. The method of claim 1 wherein said B-component is hydrophilic.

16. The method of claim 1 wherein said A-component is hydrophobic and said B-component is hydrophilic.

17. The method of claim 1 wherein said composite sheet comprises:

an A-component layer which is melted and resolidified;

an A/B-component layer in which said A-component and said B-component are sintered together; and a B-component layer.

18. The method of claim 1 wherein at least about 50% of said A-component is melted and migrates into said A/B-component layer during the sintering step.

19. The method of claim 1 wherein said A-component is a non-woven fabric sheet comprising meltable synthetic fibers.

20. The method of claim 1 wherein said A-component is a non-woven fabric sheet comprising polyolefin fibers.

21. The method of claim 1 wherein said A-component comprises a non-woven fabric sheet of microfibers having a diameter of 1.5 mm or less.

22. The method of claim 1 wherein said first layer is corrugated with a plurality of crests and troughs intermittently formed across said first layer, and said first and second layers are sintered at said troughs in said sintering step.

23. The method of claim 1 wherein said A-component and said B-component are selected from the group consisting essentially of synthetic fibers, chemical fibers and regenerated fibers.

24. The method of claim 1 wherein said A-component comprises non-woven bicomponent fibers having a sheath material with the first melting temperature and a heat resistant polymer core material with a melting point higher than the first melting temperature.

25. The method of claim 1 wherein said A-component comprises melt-blown polyolefin and said B-component comprises a non-woven spunbond bicomponent fiber of polyethylene sheath and polyester core.

26. The method of claim 1 wherein said A-component comprises a wet-formed web of synthetic polyolefin and said B-component comprises a non-woven spunbond bicomponent web having polyethylene sheath and polyester core.

* * * * *